United States Patent [19]

Edwards et al.

[11] Patent Number: 5,472,441
[45] Date of Patent: * Dec. 5, 1995

[54] DEVICE FOR TREATING CANCER AND NON-MALIGNANT TUMORS AND METHODS

[75] Inventors: Stuart D. Edwards, Los Altos; Ronald G. Lax, Grass Valley, both of Calif.

[73] Assignee: Zomed International, Mountain View, Calif.

[*] Notice: The portion of the term of this patent subsequent to Oct. 17, 2012, has been disclaimed.

[21] Appl. No.: 208,676

[22] Filed: Mar. 11, 1994

Related U.S. Application Data

[63] Continuation-in-part of Ser. No. 148,439, Nov. 8, 1993, Pat. No. 5,458,597.

[51] Int. Cl.⁶ .................................................. A61B 17/36
[52] U.S. Cl. ............................... 606/41; 606/49; 604/21; 128/898
[58] Field of Search ................................. 606/41, 45–52; 604/21; 128/898

[56] References Cited

U.S. PATENT DOCUMENTS

| | | |
|---|---|---|
| 3,474,777 | 10/1969 | Figge et al. . |
| 3,987,795 | 10/1976 | Morrison . |
| 4,033,351 | 7/1977 | Hetzel . |
| 4,043,342 | 8/1977 | Morrison, Jr. . |
| 4,303,636 | 12/1981 | Gordon . |
| 4,331,654 | 5/1982 | Morris . |
| 4,345,588 | 8/1982 | Widder et al. . |
| 4,506,680 | 3/1985 | Stokes . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman ..................................... 606/50 |
| 4,574,782 | 3/1986 | Borrelli et al. . |
| 4,586,490 | 5/1986 | Katz . |
| 4,652,257 | 3/1987 | Chang . |
| 4,662,359 | 5/1987 | Gordon . |
| 4,690,130 | 9/1987 | Mirell . |
| 4,692,139 | 9/1987 | Stiles . |
| 4,753,248 | 6/1988 | Engler et al. . |
| 4,763,671 | 10/1988 | Goffinet . |
| 4,776,086 | 10/1988 | Kasevich et al. . |

(List continued on next page.)

FOREIGN PATENT DOCUMENTS 2-121675  5/1990  Japan .

*Primary Examiner*—Stephen C. Pellegrino
*Assistant Examiner*—Michael Peffley
*Attorney, Agent, or Firm*—Haynes & Davis

[57] ABSTRACT

A method of this invention for treating body tissues containing cancerous cells or non-malignant tumors with RF ablation, alone or in combination with systemic or localized chemotherapy comprising introducing a stylet comprising an electrode surface and a sleeve longitudinally moveable thereon into the vicinity of the body tissues, retracting the sleeve from a portion of the electrode surface, and supplying RF power to the electrode surface sufficient to heat the tissue to a temperature of above about 45° C. for a time to cause reduction of tissue mass in the vicinity of the electrode. The RF power supplied to the electrode surface is sufficient to effect a desiccated fluid diffusion barrier capsule surrounding the body tissue being treated. The stylet can include a hollow tube having fluid distribution ports therein, and the method can include the step of passing fluid through one or more distribution ports into the body tissue being treated. The fluid can be saline or a chemotherapeutic fluid such as liquid or gas containing a cytotoxic agent, for example. The fluid can be administered in a variety of procedures. The fluid can be passed through a distribution port into the body tissue before, during and/or after the RF power is supplied to the electrode surface, for example. Preferably, the fluid is introduced after a barrier capsule has been formed. The devices comprises electrodes havming a hollow core and a closed sharpened distal tip. The electrode has a plurality of fluid distribution ports therein for distribution of fluid treatment agents into the tissue.

9 Claims, 16 Drawing Sheets

U.S. PATENT DOCUMENTS

| | | |
|---|---|---|
| 4,800,899 | 1/1989 | Elliott . |
| 4,813,429 | 3/1989 | Eshel et al. . |
| 4,818,542 | 4/1989 | DeLuca et al. . |
| 4,823,793 | 4/1989 | Angulo et al. . |
| 4,860,744 | 8/1989 | Johnson et al. . |
| 4,907,589 | 3/1990 | Cosman . |
| 4,920,978 | 5/1990 | Colvin . |
| 4,931,047 | 6/1990 | Broadwin et al. . |
| 4,945,912 | 8/1990 | Langberg . |
| 4,947,842 | 8/1990 | Marchosky et al. . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,989,601 | 2/1991 | Marchosky et al. . |
| 5,007,908 | 4/1991 | Rydell ................................. 606/50 |
| 5,009,656 | 4/1991 | Reimels . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 10/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,084,001 | 1/1992 | Van't Hooft et al. . |
| 5,084,045 | 1/1992 | Helenowski . |
| 5,085,659 | 2/1992 | Rydell . |
| 5,100,423 | 3/1992 | Fearnot . |
| 5,125,928 | 6/1992 | Parins et al. . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. ............................. 606/41 |
| 5,183,455 | 2/1993 | Hayman et al. . |
| 5,190,539 | 3/1993 | Fletcher et al. . |
| 5,190,541 | 3/1993 | Abele et al. ............................. 606/49 |
| 5,190,766 | 3/1993 | Ishihara . |
| 5,197,466 | 3/1993 | Marchosky et al. . |
| 5,197,963 | 3/1993 | Parins ..................................... 606/50 |
| 5,197,964 | 3/1993 | Parins . |
| 5,203,782 | 4/1993 | Gudov et al. . |
| 5,205,289 | 4/1993 | Hardy et al. . |
| 5,207,675 | 5/1993 | Canady . |
| 5,217,458 | 6/1993 | Parins . |
| 5,236,410 | 8/1993 | Granov et al. . |
| 5,236,424 | 8/1993 | Imran . |
| 5,246,438 | 9/1993 | Langberg . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,286,253 | 2/1994 | Fucci . |
| 5,290,286 | 3/1994 | Parins . |
| 5,295,955 | 3/1994 | Rosen et al. . |
| 5,300,069 | 4/1994 | Hunsberger et al. . |
| 5,300,099 | 4/1994 | Rudie . |
| 5,322,503 | 6/1994 | Desai ..................................... 604/21 |

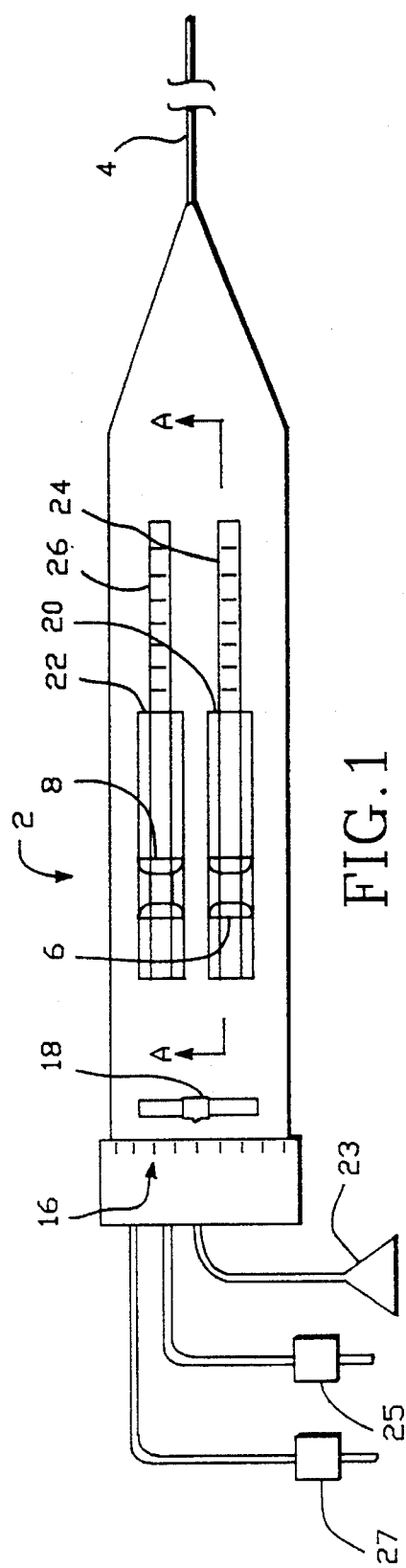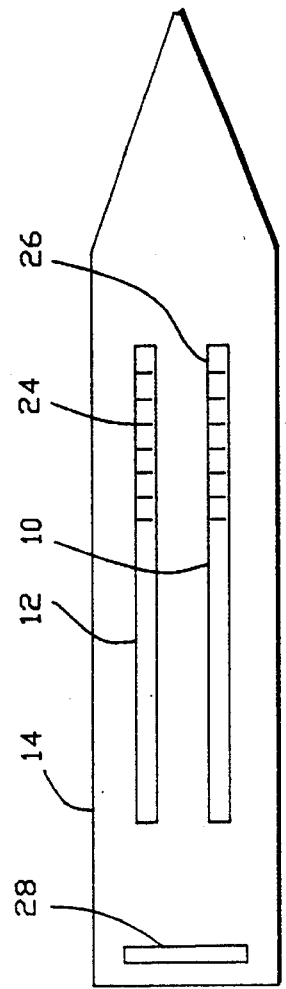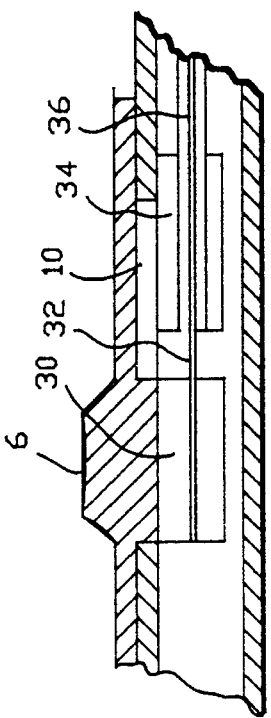

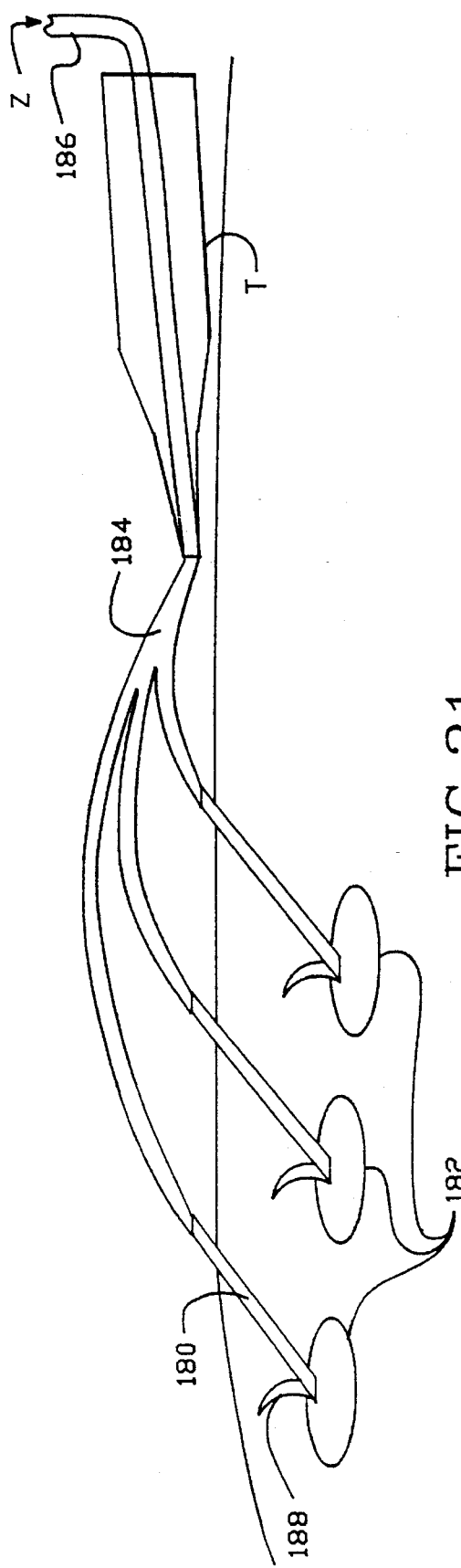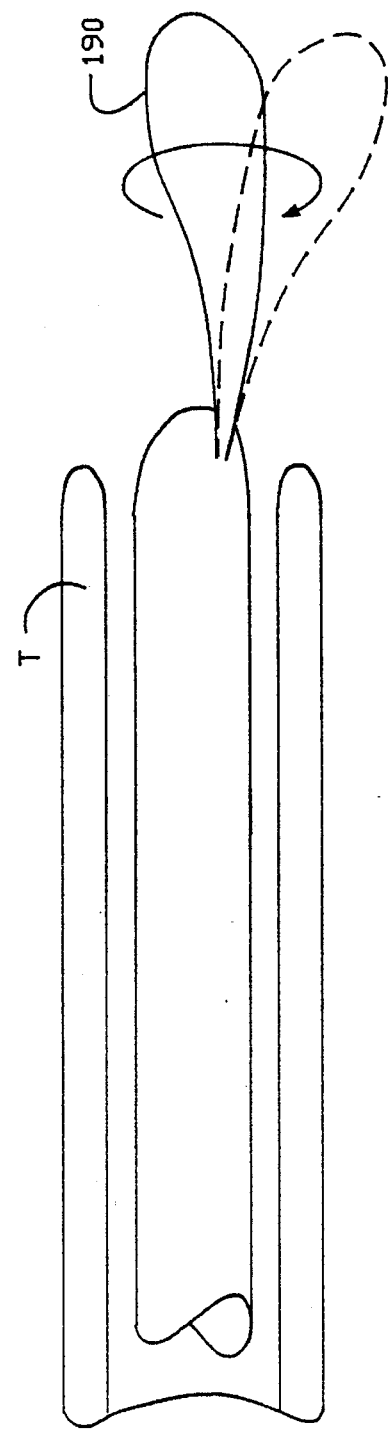
FIG. 21
FIG. 22

DEVICE FOR TREATING CANCER AND NON-MALIGNANT TUMORS AND METHODS

CROSS-REFERENCES TO RELATED APPLICATIONS

This application is a continuation-in-part of copending U.S. Ser. No. 08/148,439, filed Nov. 8, 1993, now U.S. Pat. No. 5,458,597, issued Oct. 17, 1995, which is related to U.S. Ser. No. 08/148,441, the entire contents of each of which are hereby incorporated by reference.

BACKGROUND OF THE INVENTION

1. Field of the Invention

This invention is directed to a novel device and method for treating body tissues which include neoplastic cells, such as cancerous tissue and non-malignant tumors, to reduce the mass thereof. The device penetrates normal tissue to reach the tissue including the neoplasm and delivers therapeutic ablative energy to the tissue and/or deliver therapeutic substances to the tissue. It limits delivery of the therapeutic treatment to the precise location selected. This device is a cannula device for positioning a treatment assembly in the area or organ containing the neoplasm with at least one stylet in the cannula, mounted for extension from the end of the cannula through surrounding tissue to the tissue targeted for medical treatment. This device is suitable for reducing the mass of any type of tissue, and it is most particularly useful for treating tissue containing neoplastic cells.

2. Discussion of the Related Art

Surgical treatment of cellular tissues usually requires direct contact of target tissue with a medical instrument, usually exposing both the target and intervening tissue to substantial trauma. Often, precise placement of a treatment probe is difficult because of the location of a target tissue in the body or the proximity of the target tissue to obstructions or easily damaged, critical body organs, nerves, or other components.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 kHz in order to avoid any adverse nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a nondestructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, tissues in organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Chemotherapy generally involves systemic delivery of the therapeutic agents, the agents affecting both normal dividing and abnormal cells. Efforts to target neoplastic cells, such as with "bullets" comprising a neoplastic preferentially binding antibody coupled with a cytotoxic agent have had limited success; the agents are removed and concentrated by the liver in the removal process, exposing the liver to high levels of the toxin. Photodynamic therapy seeks to limit the cytotoxic activity to the areas exposed to light energy; however, since the photodynamic agents are administered systemically, epidermal areas exposed to light are also affected, requiring protection from the sun until the photodynamic agents are eliminated from the body.

OBJECTS AND SUMMARY OF THE INVENTION

It is one object of this invention to provide a device and method for treating body tissues containing neoplastic tissue such as cancerous tissue and non-malignant tumors to reduce the mass thereof.

It is another object of this invention to provide a device for combined therapeutic ablation and chemotherapy which forms an infusion barrier surrounding the tissue to be treated, the barrier substantially confining liquid treatment agents administered by the device to the zone within the capsule of the infusion barrier.

It is a further object of this invention to provide a device for therapeutic ablation and chemotherapy which increases distribution of therapeutic agents through target tissue by use of the ablative heat, alternating with or concurrent with tissue ablation.

It is a still further object of this invention to stimulate reduction of neoplastic cells in an organ or body tissue containing one or more neoplastic sites by applying therapeutic ablative energy to a portion of the organ or body tissue, alone or in combination with the application of chemotherapy.

In summary, the method of this invention for treating body tissues containing cancerous cells or non-malignant tumors comprises a) introducing a stylet comprising an electrode surface and a sleeve longitudinally moveable thereon into the vicinity of the body tissues, b) retracting the sleeve from a portion of the electrode surface, and c) supplying RF power to the electrode surface sufficient to heat the tissue to a temperature of above about 45° C. for a time to cause reduction of tissue mass in the vicinity of the electrode.

In one embodiment of the method, the RF power supplied to the electrode surface is sufficient to form a desiccated fluid diffusion barrier capsule surrounding the body tissue being treated.

Preferably, the stylet includes a hollow tube having fluid distribution ports therein, the tube comprising a fluid supply means. The method includes the step of passing fluid through distribution ports into the body tissue being treated. The fluid can be saline or a chemotherapeutic fluid such as liquid containing a cytotoxic agent or a cytotoxic gas, for example.

The fluid can be administered in a variety of procedures. The fluid can be passed through the distribution ports into the body tissue before, during and/or after the RF power is supplied to the electrode surface, for example. Preferably, fluid is introduced after a barrier capsule has been formed.

In summary, a medical ablation device of this invention for treating tissues containing cancerous cells and for treating non-malignant tumors comprises a tubular RF electrode for reducing mass of the tissues by ablative treatment. The electrode can have a hollow core and a closed, sharpened distal tip, the electrode being enclosed in an insulating sleeve which is optionally longitudinally moveable thereon. The electrode can have a plurality of fluid distribution ports therein for distribution of fluid treatment agents into the tissue. Optionally, the device can include a tube within the electrode and axially concentric therewith, the tube being axially moveable in the electrode to block or close selected fluid distribution ports and prevent fluid passage therethrough.

One embodiment of this invention is a medical ablation device with an electrode, the electrode comprising a support tube. The outer surface of the support tube can support a plurality of conductive and electrically isolated sleeve segments adjacent to one another, each conductive sleeve segment being connected to a source of RF power. Each sleeve segment can be separated from and insulated from an adjacent sleeve segment 4 by an annular insulator, the space between each annular insulator and an adjacent sleeve comprising a gas distribution outlet. The support can have fluid distribution ports, each fluid distribution port being positioned under an annular insulator, whereby fluid passing through each fluid distribution port passes outward through a gas distribution outlet. Optionally, the device can include an outer sleeve means extending over the conductive sleeves and annular insulators, the outer sleeve being longitudinally moveable thereon for blocking selected gas distribution outlets.

As a further aspect of the invention, the ablative device includes a plurality of electrodes, wherein the device can work in either a bi-polar mode or a mono-polar mode. The mode selected will depend upon the nature of the target area, for example, the size, shape or location of the cells to be attacked. When in the bi-polar mode, one or more of the electrodes of the device will be charged positively, with one or more of the remaining electrodes being charged negatively so that an ablative field is created between two or more of the electrodes of the device. In the mono-polar mode, one or more of the electrodes will be charged with a given polarity and the targeted tissue will be positioned between these electrodes and a ground plane which will function as the other electrode. According to this embodiment, the RF energy supply can alternate between the bi-polar and mono-polar modes.

As another embodiment according to the present invention, an electrode netting is provided within a trocar such that it is tightly squeezed to a constricted shape while inside the trocar, whereas when it is pushed out of the hollow trocar, it will expand and have a pliant texture to be pressed into resilient contact with the surface of an organ such as, for example, lung tissue. The advantage of this embodiment is that the pliant electrode netting can be snugly pressed into the peaks and valleys constituting an irregular surface such as the surface of a patient's lung.

As a still further embodiment according to the present invention, an ablative device including one or more electrodes is moved slightly within the targeted tissue so as to increase the length of time for which heating of the tissue can occur. This leads to a delay in the onset of desiccation immediately adjacent to the electrode. In the conventional devices, once the tissue surrounding the electrode becomes desiccated, the impedance between the electrodes becomes great enough to cut off the flow of current between the electrodes, i.e., the dehydrating of the tissues acts as a type of natural "switch" which stops the current between the active electrode and the indifferent (neutral) electrode because of the decrease in conductivity of the current transfer medium. By moving the electrode slightly within the tissue, the ablation time can be increased which in turn leads to an increase in the resulting ablation volume.

As another embodiment of the present invention, chemotherapeutic drugs are delivered to the targeted tissue in the form of encapsulated microspheres. These microspheres are porous and coated with a material which can be dissolved using either a solvent or ablative RF energy. This has been shown to provide a convenient way of administering therapeutic drugs to the cancerous tissue by accurately pinpointing the location to be treated, injecting the microspheres and then releasing the drugs from the microsphere at any desired time by applying the solvent or ablative energy to the surrounding coating.

Another novel feature of the present invention involves the simultaneous delivery of chemotherapeutic drugs to a number of isolated points of a patient's organ or skin, whereby a small pump is used to deliver the drugs in a site-specific manner through the use of a plurality of thin capillary type tubes. This provides the important advantage of only applying the therapeutic compounds to the cancerous sites rather than throughout the entire organ or the entire body of the patient. By confining the drugs to the specific cancerous portions, a much lower dose of chemotherapy can be applied at any given time with respect to the entire patient's body, while at the same time in a much greater concentration with respect to the cancerous sites. This can provide the important advantage of shorter treatment periods as opposed to conventional methods.

As a further embodiment according to the invention, a small wire or monofilament loop can be used to further liquefy ablated tissue which has undergone ablative treatment with RF energy. The wire or monofilament loop is designed to be soft enough so that only the already partially liquefied tissue will be affected by the "whipping" motion of the loop as it undergoes rotation, while normal tissue will not be damaged thereby. Once the ablated tissue is further liquefied, it becomes easier to remove this tissue by suctioning and flushing methods, as opposed to allowing the body to remove the tissue by way of normal body processes using the kidney and/or liver. This has the important advantage of assisting the body in removing the cancerous tissue by reducing the load on the kidneys and/or liver.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a planar view of a stylet ablation device of this invention.

FIG. 2 is a top view of the handle top plate of the stylet ablation device shown in FIG. 1.

FIG. 3 is a fragmentary cross-sectional view of the manual control portion of the handle of the stylet ablation device shown in FIG. 1, taken along the line A—A in FIG. 1.

FIG. 21 illustrates another embodiment of the invention which shows the manner by which a therapeutic substance can be applied to a plurality of isolated sites on an organ of the patient or, alternatively, on the patient's skin surface.

FIG. 22 illustrates another embodiment according to the invention whereby a monofilament wire or loop is used as a type of whip for liquefying ablated tissue within the patient for subsequent removal thereof.

DETAILED DESCRIPTION OF THE PREFERRED EMBODIMENTS

Figure 4:
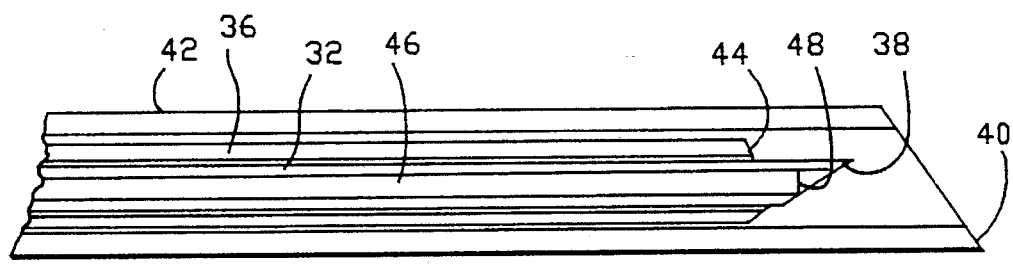
FIG. 4 is a fragmentary cross-sectional view of the tip of the stylet ablation device such as that shown in FIG. 1 with the stylet retracted into the tip.

The medical ablation devices of this invention are uniquely superior for localized therapeutic ablation to remove or reduce undesired tissue masses from remote locations in the body. With suitably shaped rigid or flexible delivery tubes, the devices can be used with conventional delivery systems including scopes such laparoscopes, cystoscopes, and the like. With delivery tubes such a needles, the device with a memory shaped electrode can be used to ablated undesired tissue in orthopedic, neurological, gynecological and for less invasive surgical applications such as near zero surgical ablation of spinal discs to alleviate encroachment and pressure from herniated disks on adjacent nerves in the spinal column.

Referring to the drawings, FIG. 1 is a planar view of a stylet ablation device of this invention. The device comprises a handle portion 2 and a delivery tube portion 4. Stylet sleeve control manual tab 6 and stylet electrode control manual tab 8 are mounted for sliding engagement in slots 10 and 12 in the handle top plate 14 (FIG. 2). Index markings 16 indicate the relative angle of orientation of the stylet with respect to the stylet angle indicator 18. Angle indicator 18 can be a bubble in a curved transparent tube, a weighted pivot dial indicator or an electronic angle indicator. The position of the distal edges 20 and 22 of the tab slides 6 and 8 with their respective gauge reference strips 24 and 26 independently indicate the relative advancement and retraction of the stylet electrode and sleeve shown in FIGS. 2–4.

Connectors for the fiber optic connector 23, RF power connector 25, and ohmic resistance detector 27 extend from the proximal end of the handle housing.

FIG. 2 is a top view of the handle top plate of the stylet ablation device shown in FIG. 1. Slots 10 and 12 receive the respective tabs 6 and 8 for sliding engagement therein. Slot 28 receives the stylet angle indicator.

FIG. 3 is a fragmentary cross-sectional view of the manual control portion of the handle of the stylet ablation device shown in FIG. 1, taken along the line A–A. Manual electrode tab 6 is attached to an electrode connector 30 which is connected to the proximal end of the stylet electrode 32. Manual sleeve tab 8 (FIG. 1) is connected to a sleeve connector 34 which is connected to the proximal end of the sleeve 36.

The electrode 32 is preferably made of a flexible, shape memory metal such as nickel-titanium alloy or tempered steel. The sleeve is made of a highly conformable insulating plastic material such as polyimide.

Simultaneous forward and rearward movement of the control tabs 6 and 8 effect simultaneous advancement and retraction of the treatment stylet. Individual movement of the control tabs 6 and 8 provide individual advancing and retracting movement of the respective sleeve and electrode. Indexing strips 24 and 26 provide reference points for controlled positioning of the sleeve control tabs 6 and 8, permitting precise, independent positioning of the stylet elements for controlled ablation of remote body portions as is explained in greater detail hereinafter.

FIG. 4 is a cross-sectional view of the tip of the stylet ablation device such as that shown in FIG. 1 with the stylet retracted into the tip for initial insertion to a position accessible with a straight needle. The electrode tip 38 is positioned behind the leading sharpened tip 40 of the needle or tube 42. The insulating sleeve tip 44 is positioned just behind the leading edge of the electrode tip 38.

When the electrode 32 is a hollow tube, it can be a conduit for aspiration during treatment, liquid delivery, or in the embodiment shown, a housing for a fiber optic 46. The polished fiber optic tip 48 is then positioned behind the electrode tip 38 to facilitate viewing of the tissue surrounding the electrode tip during insertion.

Figure 5:
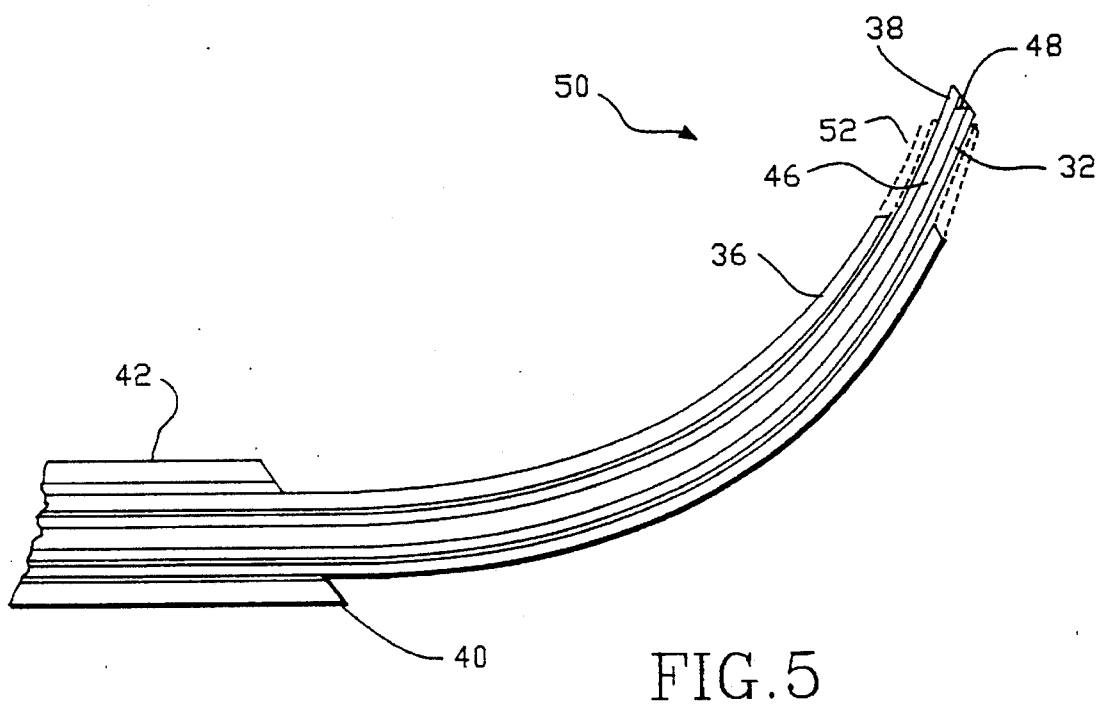
FIG. 5 is a fragmentary cross-sectional view of the tip of the stylet ablation device shown in FIG. 4 with a flexible stylet having a predetermined curved configuration with the electrode and sleeve extended from the tip.

FIG. 5 is a cross-sectional view of the tip of the stylet ablation device shown in FIG. 4 with the electrode and sleeve extended. This embodiment shows a flexible stylet 50 having a predetermined curved configuration. The flexible stylet can also be straight, if the remote position can be reached by a straight path from the point of entry without damaging a vital body component. The electrode can be made of a shape memory alloy, shaped to revert to a desired configuration when released from the tubing. The configuration can be simple curves, a combination of straight portions and curves, curves with differing radii, in two or three dimensions, selected to direct the electrode and its surrounding flexible, highly conformable sleeve in a preselected two or three dimensional path through tissue to a site to be ablated.

Methods for shaping shape memory alloys are well known in the art and are not a part of this invention. In general, the alloys are annealed with heat and then set in the desired memory shape by quick cooling the annealed electrode while maintaining it in the non-linear shape ultimately desired.

The sleeve 36 is initially in the dotted line position 52. Following insertion into the body to the specific site to be ablated, the sleeve 36 is withdrawn from a selected portion of the electrode 32 to the solid line position to expose the specific electrode area required to form a lesion of the desired size.

A method of this invention for medical ablation of difficult to access tissues comprising first inserting a hollow needle through a tissue layer, the needle enclosing a conductive electrode of highly flexible memory metal having a predetermined curved memory configuration and a sharpened distal terminus, the electrode tube being enclosed within an insulating sleeve axially moveable thereon and bendable therewith. Then the electrode and sleeve are advanced from the terminal end of the hollow needle, whereby the portion of the electrode and sleeve advanced beyond the end of the needle adopt the predetermined curved memory configuration and the electrode and sleeve follow a correspondingly predetermined curved path through tissue to the site to be ablated. Then a portion of the sleeve is withdrawn from the terminus of the electrode to expose a predetermined electrode area for ablation. Finally, RF energy is applied to the tissue surrounding the exposed electrode area to effect ablation thereof.

Figure 6:
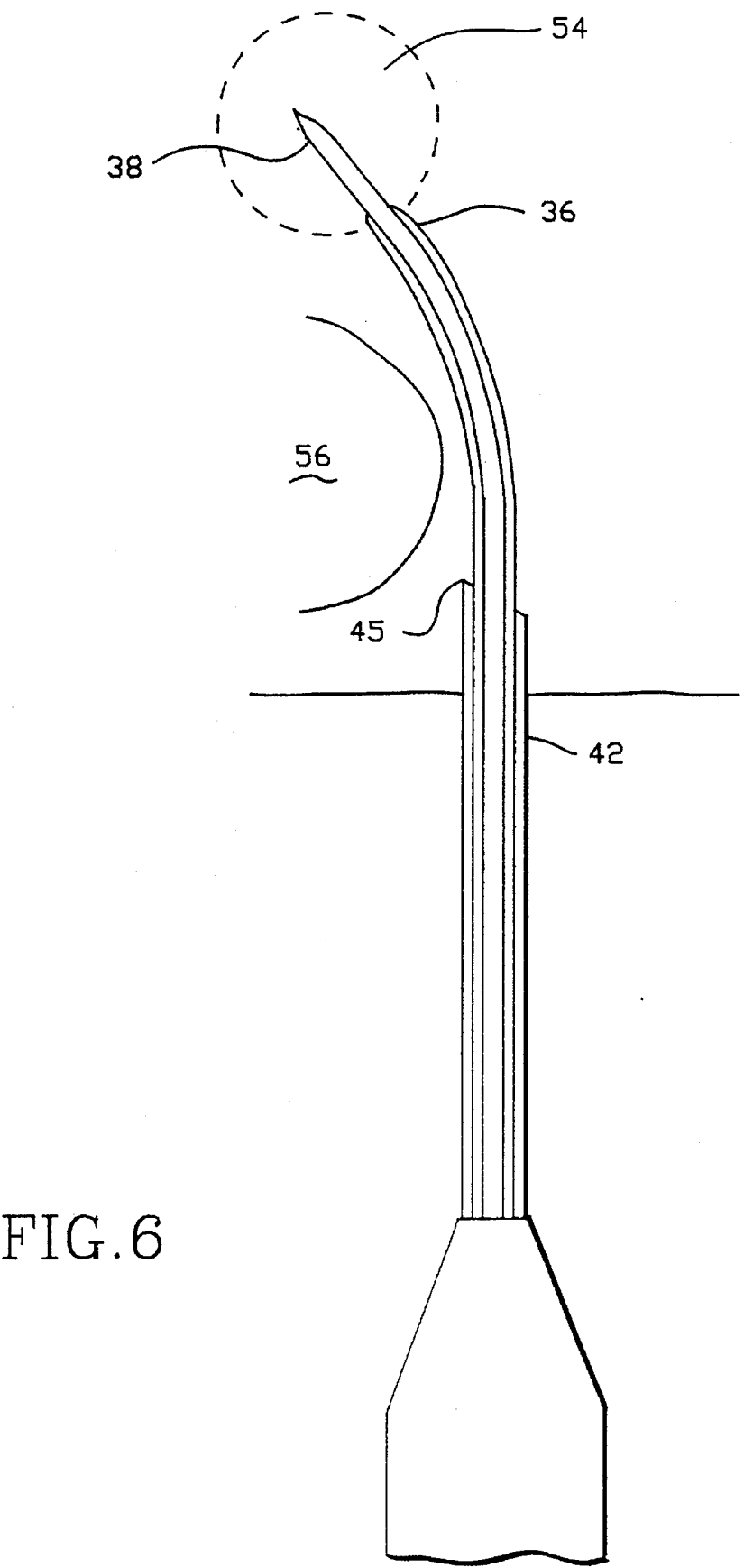
FIG. 6 is a schematic view showing use of an embodiment with a shape memory electrode preformed into a curved shape to ablate a tissue mass behind an obstacle such as a vertebra.

Referring to FIG. 6, another embodiment of the invention uses a shape memory electrode preformed into a curved shape to ablate a near zero access area behind an obstruction in the body. The objective of the treatment is to reduce the size of the mass 54 behind a rigid obstacle such as bone 56 (or area to be protected from penetration). The electrical conductor and sleeve is extended from the needle 40 through surrounding tissue around the obstacle to its back surface, and the target tissue to be reduced. The sleeve 36 is then withdrawn to a position exposing the electrode area required to ablate the tissue mass. Heat is generated in the target tissue from an electric current or electromagnetic field produced by the electrical conductor. Preferably, the volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated. The current passes to a large surface area grounding plate contacting the outer skin surface.

Figure 7:
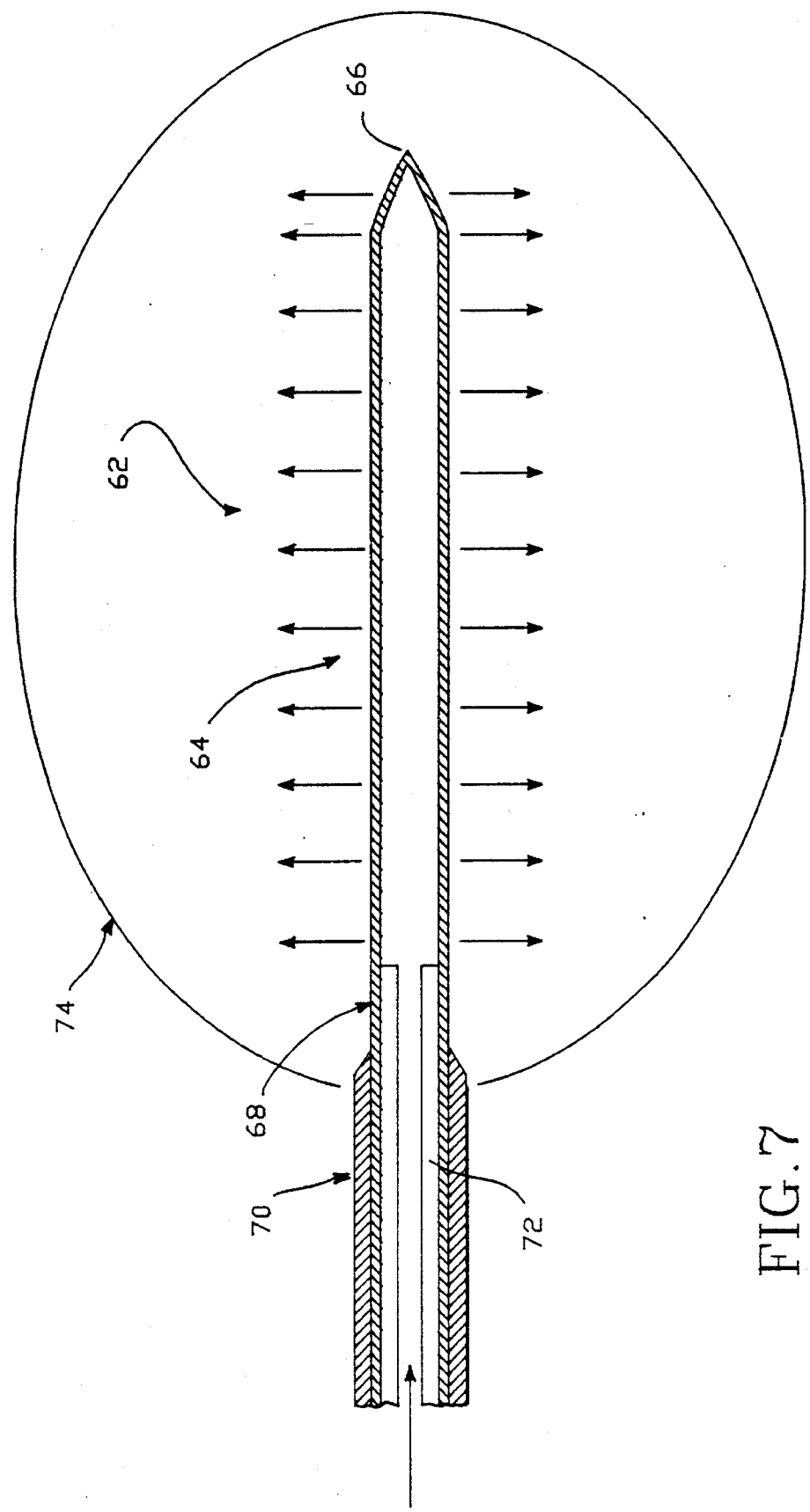
FIG. 7 is a cross-sectional view of a RF stylet including chemotherapy agent distributors.

FIG. 7 is a cross-sectional view of a RF stylet including chemotherapy agent distributors of this invention. In this embodiment, the stylet 60 includes an electrode 62 having the configuration of a tube 64 with a sharp-tipped, closed distal end 66 and a plurality of fluid outlet openings 68, distributed along the length of the exposed electrode portion. The electrode 62 is enclosed within an insulating sleeve 70 which is longitudinally slidable on the electrode, as described above, to control the length and surface of electrode exposed to the surrounding tissue. The tube can optionally contain an inner unperforated tube 72, the position of which can be adjusted to expose a selected number of fluid distribution ports. The treatment fluid flows outwardly through the distribution ports as shown by the arrows extending outwardly therefrom.

The stylet 60 is advanced to the tissue to be ablated, and the sleeve 70 is withdrawn, exposing a controlled length of electrode and selected number of fluid distribution ports. RF energy is applied, raising the temperature in the lesion site to a temperature of above 45° C. For creating an infusion barrier capsule 74, the temperature can be from about 45° C. to 170° C. and is preferably from about 80° C. to 120° C. The desiccation boundary 74 acts as a barrier to fluid flow, forming a capsule and restraining escape of fluid introduced through the ports.

In one embodiment of the method of this invention, the infusion boundary is created before fluid is introduced, to restrain its escape from beyond the ablation zone. In another embodiment, the fluid introduction precedes or is concurrent with the application of RF energy, whereby the heating facilitates and increases the penetration of the tissue by the chemotherapeutic fluid. It will be readily apparent to a person skilled in the art that other variations and sequences, and repetitions thereof, can be applied within the scope of this invention to control the zone of treatment and fluid delivery according to the physician's desired objective.

Figure 8A:
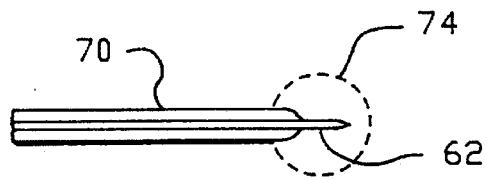
FIGS. 8a, 8b and 8c are schematic views of tissue undergoing capsular ablation according to this invention, demonstrating sleeve adjustments of the device of FIG. 7 to effect a desired ablation lesion geometry.
Figure 8B:
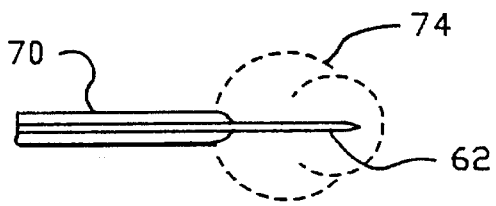
Figure 8C:
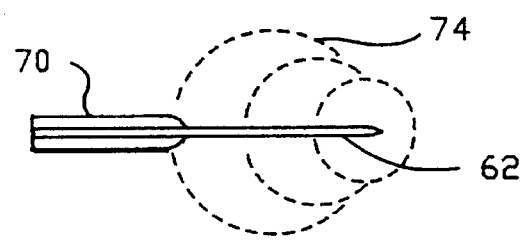

FIGS. 8a, 8b and 8c are schematic views of tissue undergoing capsular ablation according to this invention, demonstrating sleeve adjustments of the device of FIG. 7 to effect a desired ablation lesion geometry. FIG. 8a shows an initial lesion formed with a short portion of electrode 62 extending beyond the insulating sleeve 70. In FIG. 8b, the sleeve 70 has been retracted to expose a longer portion of electrode 62, producing a lesion with a larger radius, pronounced in the portion which beyond the infusion barrier formed in the ablation of FIG. 8a. In FIG. 8c, the sleeve 70 has been retracted to expose a still longer portion of electrode 62, producing a lesion with a still larger radius, pronounced in the portion which beyond the infusion barriers formed in the ablations of FIGS. 8a and 8b. The ultimate lesion barrier has an approximately overall conical configuration.

Figure 9A:
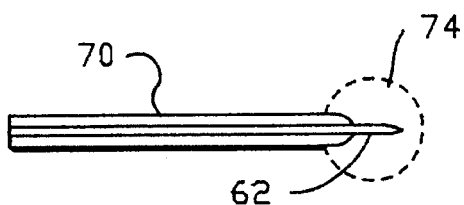
FIGS. 9a, 9b, 9c and 9d are schematic views of tissue undergoing capsular ablation according to this invention, demonstrating stylet position adjustment of the device of FIG. 7 to effect a desired ablation lesion geometry.
Figure 9B:
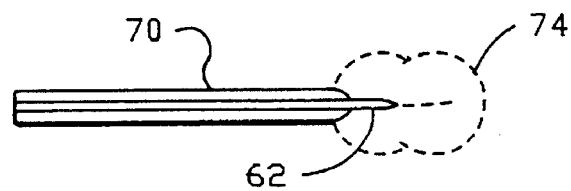
Figure 9C:
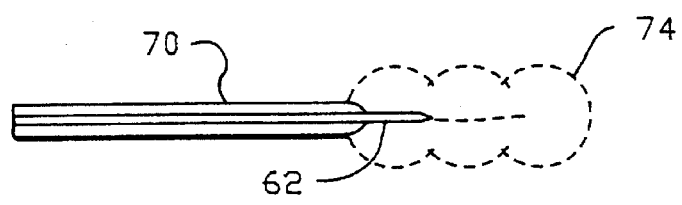
Figure 9D:
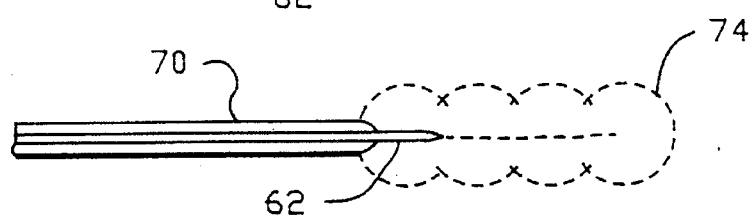

FIGS. 9a, 9b, 9c and 9d are schematic views of tissue undergoing capsular ablation according to this invention, demonstrating stylet position adjustment of the device of FIG. 7 to effect a desired ablation lesion geometry. FIG. 9a shows an initial ablation lesion formed with the stylet extending to a maximally distal position and with a small portion of the electrode 62 extended beyond the insulating sleeve 70. FIGS. 9b, 9c and 9c show successive positions and overlapping lesions formed by incrementally retracting the stylet in the proximal position, performing an ablation at each incremental position to provide an ultimate lesion barrier having an approximately overall cylindrical configuration.

It will be readily apparent to a person skilled in the art that other sequences, including combinations of sequences illustrated in FIGS. 8a, 8b and 8c, and in FIGS. 9a, 9b and 9c can be devices without departing from the spirit and scope of this invention, and all of these combinations and variations are considered to be within the scope of this invention.

Figure 10:
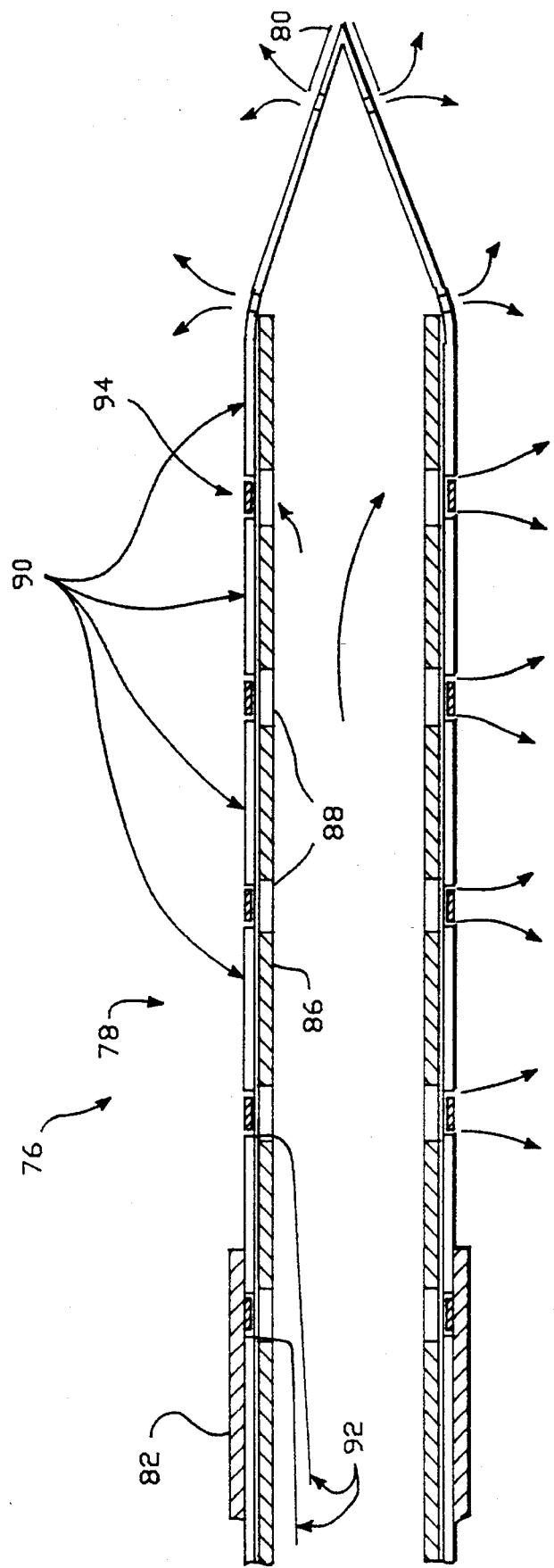
FIG. 10 is a cross-sectional view of an alternate embodiment of a RF stylet including chemotherapy agent distributors and a plurality of annular electrode conductors.

FIG. 10 is a cross-sectional view of an alternate embodiment of a RF stylet including chemotherapy agent distributors and a plurality of annular electrode conductors. In this embodiment, the stylet 76 comprises an electrode and distribution outlet bearing section 78 with a closed sharpened tip 80 and an insulating sleeve 82 longitudinally moveable thereon. The electrode section comprises an inner support tube 86 with fluid distribution ports 88 spaced along its length. Between each pair of ports 88 are positioned conductive sleeve segments or annular coatings 90. Each conductive sleeve segment 90 is connected to an individual insulated electrical RF power lead 92 connected to a switching and power delivery console (not shown). Suitable power supplies are described in copending application Ser. No. 08/061,072 filed May 14, 1993, the entire contents of which are hereby incorporated by reference. Between each conductive sleeve segment 90 is positioned an annular insulating sleeve or ring 94. Fluid passing outwardly through the ports 88 pass between the conductive sleeves segments 90 and the insulating rings 94 to pass outward into the surrounding tissue as shown by the arrows extending outwardly from the spaces between the sleeve segments 90 and rings 94.

Figure 11:
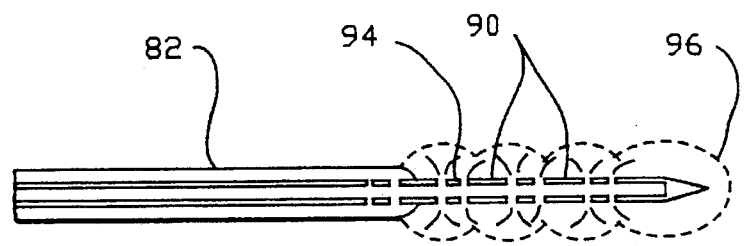
FIG. 11 is a schematic view of tissue undergoing capsular ablation according to this invention, demonstrating a monopolar ablation with a plurality of electrodes with the embodiment shown in FIG. 10 to provide an approximately cylindrical ablation barrier capsule.

FIG. 11 is a schematic view of tissue undergoing capsular ablation according to this invention, demonstrating a monopolar ablation with a plurality of electrodes with the embodiment shown in FIG. 10 to provide an approximately cylindrical ablation barrier capsule. In this embodiment, the power leads are delivering power to each conductive sleeve 90, causing current to pass outwardly from each sleeve through the surrounding tissue. This forms a roughly spherical, overlapping ablation barrier 96 around each conductive sleeve, producing a roughly cylindrical ablation barrier capsule within which the optional treatment fluids are restrained or contained.

Figure 12:
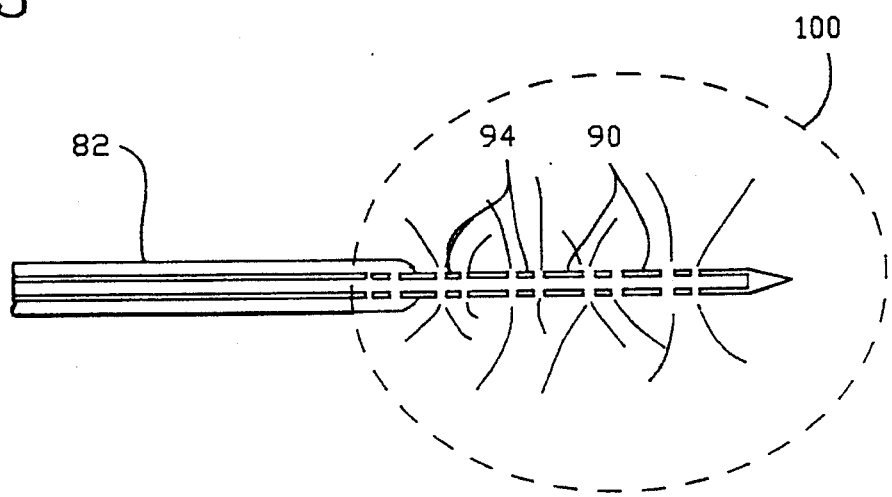
FIG. 12 is a schematic view of tissue undergoing capsular ablation according to this invention, demonstrating extended monopolar mode applications with the embodiment shown in FIG. 10 to effect an encapsulated combined ablation and chemotherapy lesion.

FIG. 12 is a schematic view of tissue undergoing capsular ablation according to this invention, demonstrating extended monopolar mode applications with the embodiment shown in FIG. 10 to effect an encapsulated combined ablation and chemotherapy lesion. In this representation, the power applied has been pulsed to effect a cause a larger overall ablation geometry, the individual ablation patterns having merged into a single elongated, larger envelope 98 for the treatment fluids.

Figure 13:
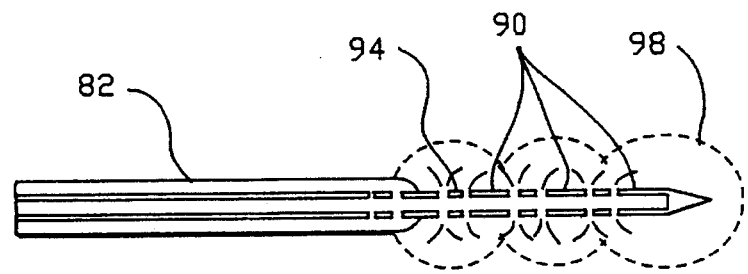
FIG. 13 is a schematic view of tissue undergoing capsular ablation according to this invention, demonstrating selection of bipolar modes with the embodiment shown in FIG. 10 to effect a desired ablation lesion geometry.

FIG. 13 is a schematic view of tissue undergoing capsular ablation according to this invention, demonstrating selection of bipolar modes with the embodiment shown in FIG. 10 to effect a desired ablation lesion geometry. The conductive sleeves 90 are connected to the power supply to effect current flow from each conductive sleeve to the conductive sleeves immediately adjacent thereto. This forms a spherical ablation diffusion barrier around each conductive path, overlapping with an adjacent sphere, and providing a roughly cylindrical ablation geometry and cylindrical infusion barrier capsule 100.

The device and method of this invention provides the physician with a flexible variety of ablation procedures, optionally combining application of ablation energy to elevate tissue temperature with the treatment zone to above 45° C. to kill cells therein, combined with fluid applications. Application of saline fluid can reduce desiccation of tissue adjacent the electrode surfaces.

Application of chemotherapeutic substances before application of the ablation energy can exploit the effects of the heating the tissue and the fluid to increase distribution of the fluid in the adjacent tissues. Application of chemotherapeutic substances after ablation forming an encapsulated lesion can reduce distribution of the chemotherapeutic agent to tissue beyond the ablation capsule, concentrating its activity to the tissues within the capsule and reducing and almost eliminating the systemic effects of the treatment. These alternatives and combinations thereof provide a wide range of alternatives to a physician treating tissue containing neoplastic cells. A treatment regimen can be devices combining any of these alternatives or all of them to increase the effectiveness of the treatment.

The ablation treatment according to this invention can be used in combination with systemic or localized chemotherapy.

Examples of chemotherapeutic agents suitable for use in the method of this invention include, but are not limited to anti-neoplastic agents. Suitable anti-neoplastic agents include, but are not limited to alkylating agents including alkyl sulfonates such as Busulfan, Improsulfan and Piposulfan; aziridines such as Benzodepa, Carboquone, Meturedepa and Uredepa; ethylenimines and Methylmelamines such as Altretamine, Triethylenemelamine, Triethylenephosphoramide, Triethylenethiophosphoramide and Trimethylolmelamine; nitrogen mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard; nitrosoureas such as Carmustine, Chlorozotocin, Fotemustine, Lomustine, Nimustine, Ranimustine; and others such as Dacarbazine, Mannomustine, Mitrobronitol, Mitolactol and Pipobroman. Also included are antineoplastic antibiotics such as Aclacinomycines, Actinomycin, Anthramycin, Azaserine, Bleomycins, Cactinomycin, Carubicin, Carzinophilin, Chromomycins, Dactinomycin, Daunorubicin, 6-Diazo- 5-oxo-L-norieucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tuberculin, Ubenimex, Zinostatin and Zorubicin. Also included are antineoplastic antimetabolites such as folic acid analogs such as Denopterin, Methotrexate, Pteropterin and Trimetrexate; purine analogs such as Fludarabine, 6-Mercaptopurine, Thiamiprine and Thioguanine; pyrimidine analogs such as Ancitabine, Azacitidine, 6-Azauridine, Carmofur, Cytarabine, Doxifluridine, Enocitabine, Floxuridine, Fluorouracil and Tegafur; enzymes such as L-Asparaginase; and others such as Aceglatone, Amsacrine, Bestrabucil, Bisantrene, Carboplatin, Cisplatin, Defosfamide, Demecolcine, Diaziquone, Eflornithine, Elliptinium Acetate, Etoglucid, Etoposide, Gallium Nitrate, Hydroxyurea, Interferon-a, Interferon-,8, Interferon-y, Interleukin-2, Lentinan, Lonidamine, Mitoguazone, Mitoxantrone, Mopidamol, Nitracrine, Pentostatin, Phenamet, Pirarubicin, Podophyllinic Acid; 2-Ethylhydrazide, Procarbazine, PSK, Razoxane, Sizofiran, Spirogermanium, Taxol, Teniposide, Tenuazonic Acid, Triaziquone, 2,2',2"-Trichlorotriethylamine, Urethan, Vinblasine, Vincristine and Vindesine.

This invention is shown by the following specific, but non-limiting examples.

EXAMPLE 1

RF Ablation Treatment of MXT Tumors

MXT tumors were implanted in 100 mice. MXT tumors were treated by RF ablation 17 days post-implantation and 30 days post-implantation. The MXT tumors show naturally intensive centro-acinar necrosis. The RF ablation power of 5, 6, and 9 watts was applied for 3, 5 and 7 minutes, and the most effective treatment was found to be with about 5.75 watts for 5 minutes.

The control group of mice was sacrificed at the same intervals as the treated group. The histological analysis follows:

1. Analysis of specimens at 0 hour post-treatment: No visible lesions.

2. Analysis of specimens at 24 hours post-treatment: no lesion.

3. Analysis of specimens at 5 days post-treatment: apparition of necrotic lesions with dedifferentiation of basal acinar layer.

4. Analysis of specimens at 15 days post-treatment:

Macroscopically: Intensive and extensive necrosis. A sole peripheral crescent of viable tumor can be seen. It depends upon the ablation electrode deployment. The 1.5 and 3 cm tumors are equally affected as the electrode deployment is viable along the tumor size.

Microscopically: Deep and almost complete destruction of MXT tumors with ghosts of necrotic glandular acini. The normal necrosis of the MXT tumors is essentially centro-acinar. In comparison, the necrosis induced by the electrode RF ablation affects the entire acini that only remains as ghosts acini but with subsisting architecture.

At the nuclear level, even the macroscopically unaffected areas, transformation of ovoid tumor nuclei in polygonal nuclei were observed.

EXAMPLE 2

Comparative Treatment of MXT Tumors with RF Ablation and/or Chemotherapy

This example shows a comparison of RF ablation, chemotherapy and a combination of RF ablation and chemotherapy in tumor area progression.

Mice were separated into four groups as follows:

1. Control—15 mice

2. Mice treated with RF ablation 17 day post-implantation—15 mice

3. Mice treated with 9 intraperitoneal chemotherapy injections of Etoposid, Cyclophosphamid and Adriablastine from day 17 post-implantation—15 mice.

4. Mice treated at day 17 with RF ablation and with 9 intraperitoneal chemotherapy injections from day 17 post-implantation with Etoposid, Cyclophosphamid and Adriablastine.

The tumor reductions differences achieved were statistically significant between evolution of control tumors and all other groups.

The most effective group was the association of chemotherapy and RF ablation with the device of this invention. The difference between RF ablation and chemotherapy was non-statistically concluant. The statistical difference between the RF ablation, alone, and the combination of chemotherapy and RF ablation favors the combination treatment.

The results shown in Examples 1 and 2 support the following conclusion:

1) RF ablation with the device of this invention is effective in decreasing tumor progression.

2) After an initial decrease at day 7 post-RF ablation treatment, tumors increase in size, indicating that a small viable tumor cell population is responsible for this increase. Two simultaneous RF ablation treatments on each side of the tumor is expected to improve the tumor reduction.

3) The RF ablation with the device of this invention enhances the chemotherapy treatment, and the combination of the chemotherapy and RF ablation produces a dramatic decrease in tumor size and a destruction of living tumor cells.

A significant advantage of being able to treat tumors such as metastatic tumors in the lung is being able to avoid the major surgery needed to obtain direct access to certain tumors. These major surgeries are extremely difficult for the patient and with general anesthesia, represent a threat to life. Indeed, certain weak, elderly and very ill patients are simply not able to stand the invasive nature of those types of surgery. The laproscopic approach offers the patient and surgeon a much more attractive and safer option. Coupled with the use of RF ablation, recovery times and hospital stays can be significantly reduced.

Figure 14:
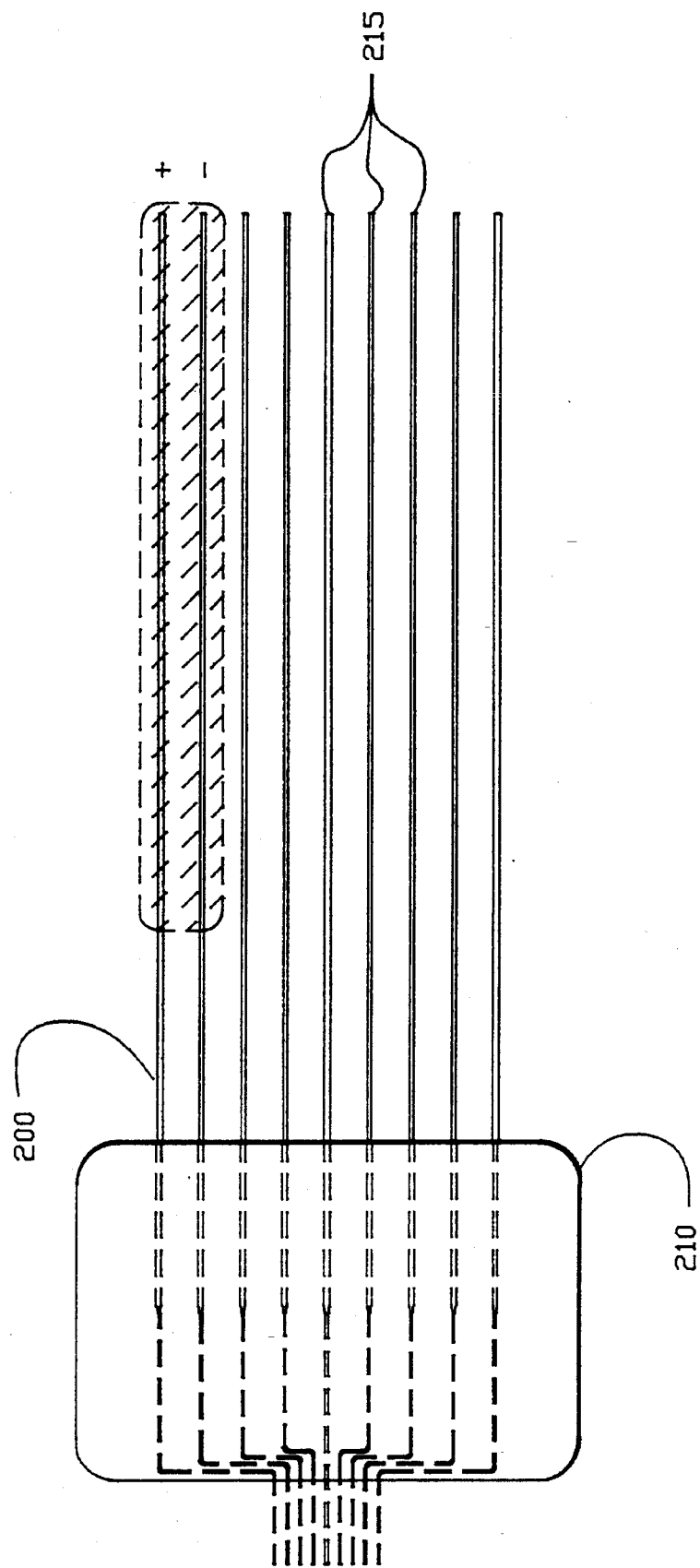
FIG. 14 shows a further embodiment according to the present invention illustrating an ablative device including a plurality of electrodes which can function in either a mono- polar mode or bi-polar mode.
Figure 15A:
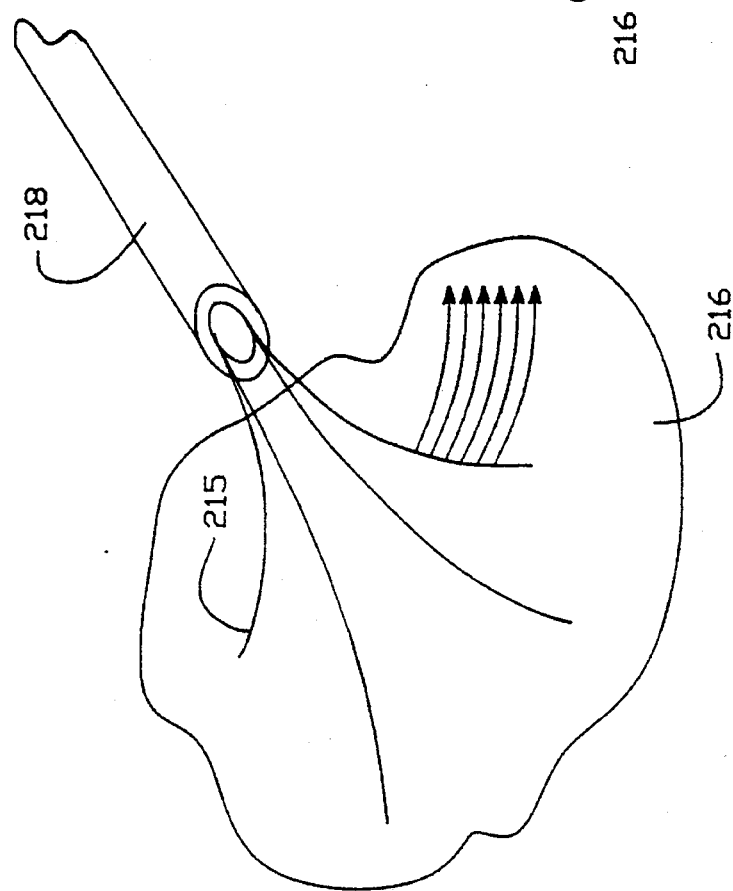
FIG. 15(a) illustrates an ablative device for use in ablating internal tissues by projecting a plurality of ablative electrodes from an end of a trocar, wherein the device works in the mono-polar mode.
Figure 15B:
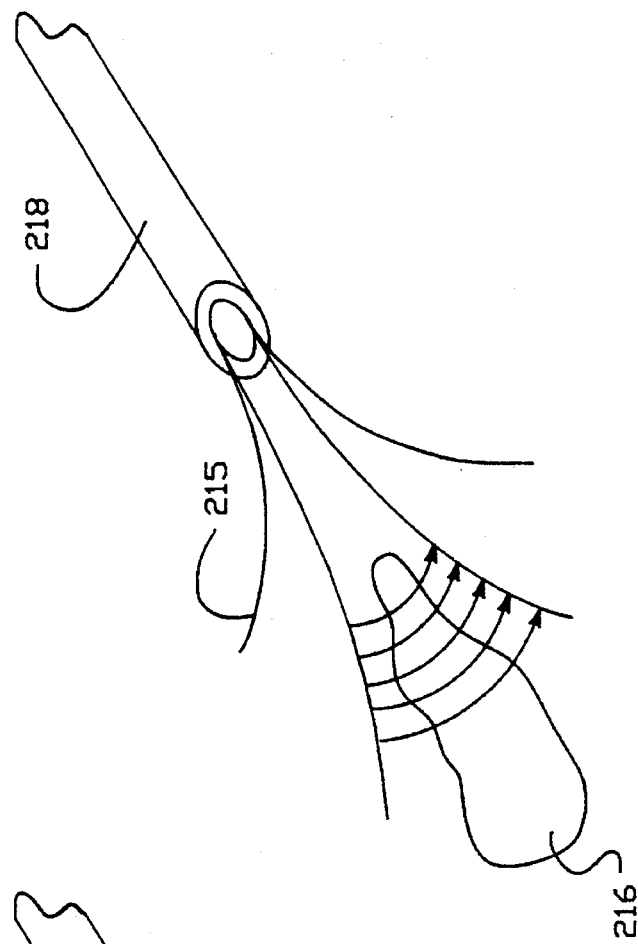
FIG. 15(b) illustrates the device of FIG. 15(a), but which works in the bi-polar mode.

As shown in FIG. 14, a further embodiment according to the present invention includes an ablative device having a catheter handle block 210 from which a plurality of ablative electrodes project. These electrodes may be solid or hollow, depending on whether therapeutic substances are to be applied to the targeted tissue through the ends of the electrodes. As shown, fixed insulation portions 200 are provided around the electrodes 215 at the portion in proximity to the catheter handle block 210. The device of FIG. 14 can operate in either the mono-polar mode or the bi-polar mode for performing ablation on targeted tissue. The particular mode selected will depend upon the type of cancerous tissue to be targeted, i.e., the size, shape or location of the targeted tissue. For example, if the cancerous site is a melanoma, it will be desirable to use the ablative device in the mono-polar mode whereby one or more of the electrodes is applied with a certain polarity and then an indifferent electrode, for example, a neutral electrode, can be provided on the opposite side of the targeted tissue so that the tissue is disposed between the electrodes 215 and the indifferent electrode. For example, the indifferent electrode may be provided on the other side of the patient's arm, leg, etc., opposite to the ablative electrodes. If, however, the targeted tissue is small enough to fit between a pair of adjacent electrodes 215, it may be desirable to charge adjacent electrodes oppositely, such as shown in FIG. 14 so that an ablative field is created between the opposite polarity electrodes. As is readily apparent, any combination of positive/ negative electrodes can be formed depending upon the size and nature of the targeted tissue. It is also pointed out that the catheter handle block can be made into any number of different configurations, i.e., the electrodes can be arranged in a circular pattern, grid pattern, zigzag pattern, etc. If it is necessary to introduce the electrodes inside the patient's body, a trocar can be used with electrodes which may be deployed outward therefrom, to be disposed in close proximity to the targeted tissue 216, as illustrated in FIGS. 15(a) and 15(b).

Figure 16:
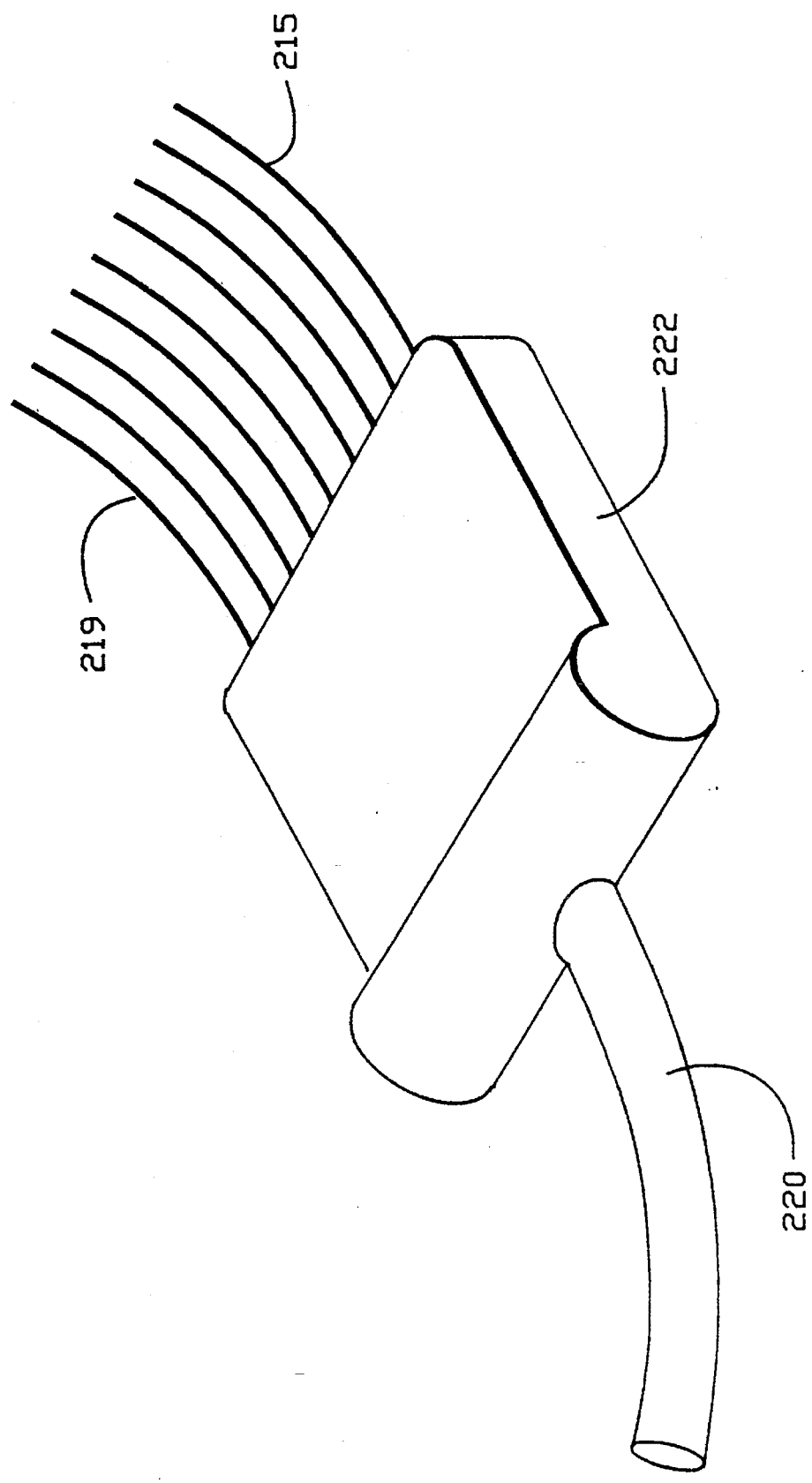
FIG. 16 illustrates an embodiment similar to that of FIG. 14 with curved electrodes and a fluid delivery tube wherein the electrodes can perform both an ablative function using RF energy and also a function of supplying therapeutic drugs through their tip portions.

As shown in FIG. 16, a cable 220 is coupled to the handle block which is provided for holding conductors and also fluid tubing for supplying therapeutic substances through the hollow curved electrodes 215. The therapeutic substances would be applied to the cancerous sites after the ablative energy is supplied with the chemotherapy acting as a type of clean-up operation in order to kill any remaining malignant cells.

Figure 17:
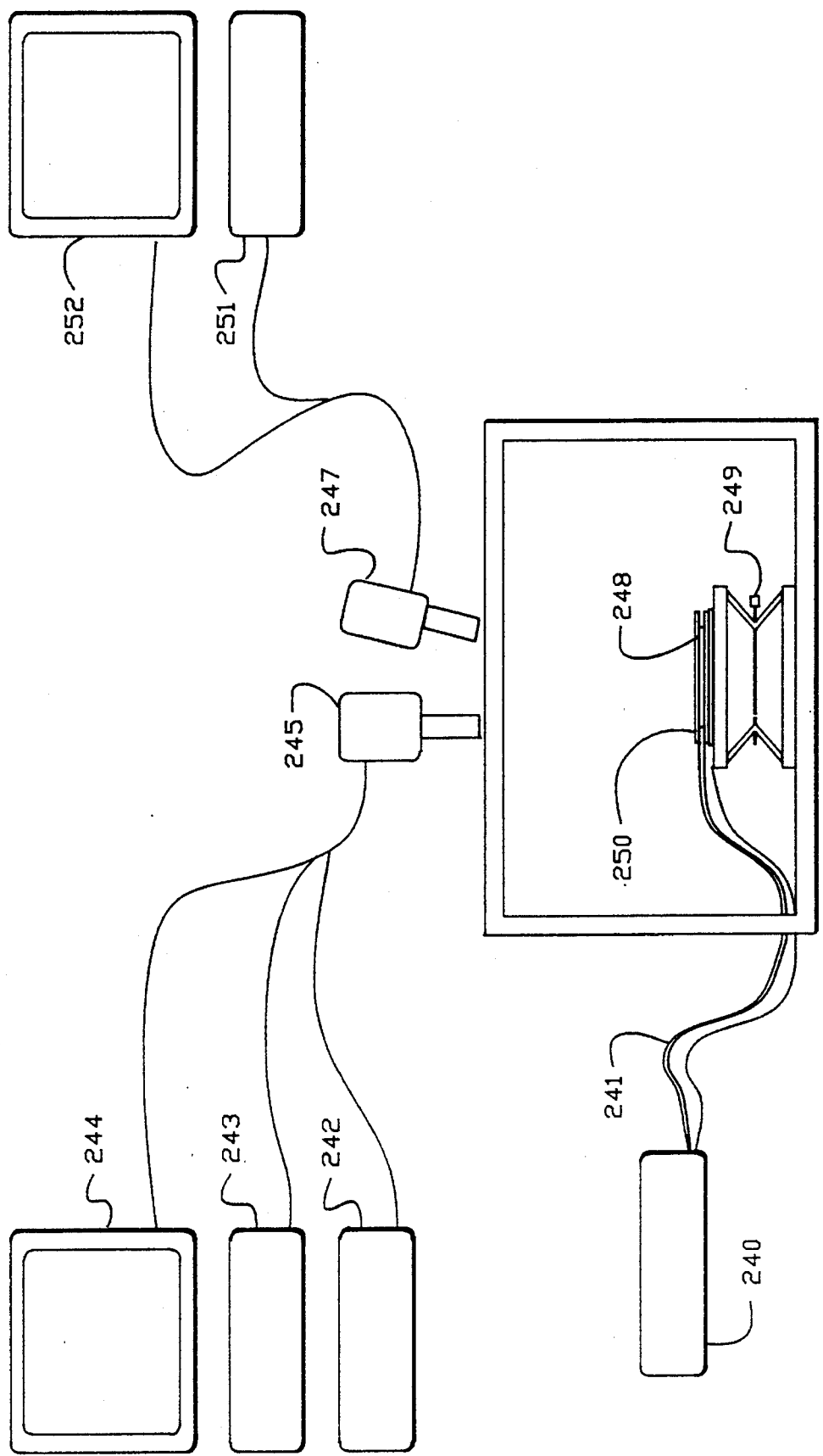
FIG. 17 illustrates a calibration technique for performing predetermined temperature and/or impedance characteristics of a sample tissue for use in actual ablation to be susequently performed on a patient.

FIG. 17 illustrates a manner by which the ablative control can be calibrated by monitoring the temperature and/or impedance levels of a piece of sample tissue as it is undergoing ablation in order to determine the most desirable amounts of heat energy to be applied to a sample such that optimal ablation can be achieved. This information can then be used in performing actual ablation within a patient. As shown, a color monitor 244, image recorder 243 and chart recorder 242 are coupled to an infrared camera 245. A video camera 247 provides an output signal to a video monitor 252 and a recorder 251. The specimen 248 which represents the sample tissue is provided on a mount and is covered by microscope slides 250. A laboratory jack 249 is used to move the specimen up or down so that the specimen is in proper focus for the video camera 247. The bi-polar leads 241 are provided to the specimen for supplying the RF energy from generator 240.

The environmental chamber is used to establish and maintain a temperature and humidity comparable to that experienced in the human body. The tissue specimen 248 will be mounted within the chamber and may be held in place under a laboratory slide. The slide will be of a thin acrylic sheet material and will hve a hole bored (not shown) in the central area, directly under the viewing area. The purpose of this slide is to retain and position the tissue specimen so that it will be in a level plane to assure that it will stay in focus for viewing by the cameras. The radio frequency generator 240 supplies RF energy via bipolar leads 241 to electrodes (not shown) into the tissue sample 248 which is positioned between microscope slides 250. The radio frequency generator is provided with a microprocessor control which monitors the tissue temperature at multiple points, monitors electrical impedance and compares the rate of change of these variables to known standards. The microprocessor control, via memory in stored algorithms will vary the power settings and time on and off (duty cycles) to accomplish desired ablation size and temperature within the ablation region.

The chart recorder 242 will be used to record the variables of time, temperature, power and impedance. The image recorder 243 will record temperature data as collected by the infrared camera 245 in the form of a color video image wherein various colors represent temperatures in the object being recorded. A color monitor is used to display the temperature image in real time (during the ablation experiment).

In order to provide a visual record of the tissue changes during ablation, the video camera 247 will provide a video signal collected from a visual position adjacent to the infrared camera. The video recorder 251 will make a record of the visual changes to the test tissue while the visual changes can be observed in a magnified image on the video monitor 252.

This experimental setup will be used to establish power, time and duty cycles to allow the researcher to formulate acceptable algorithms for optimum tissue ablation. By using various organ tissues from human cadavers, accurate predictions can be made related to the therapeutic protocol to employ in clinical trials which will finally lead to human therapy.

Figure 18:
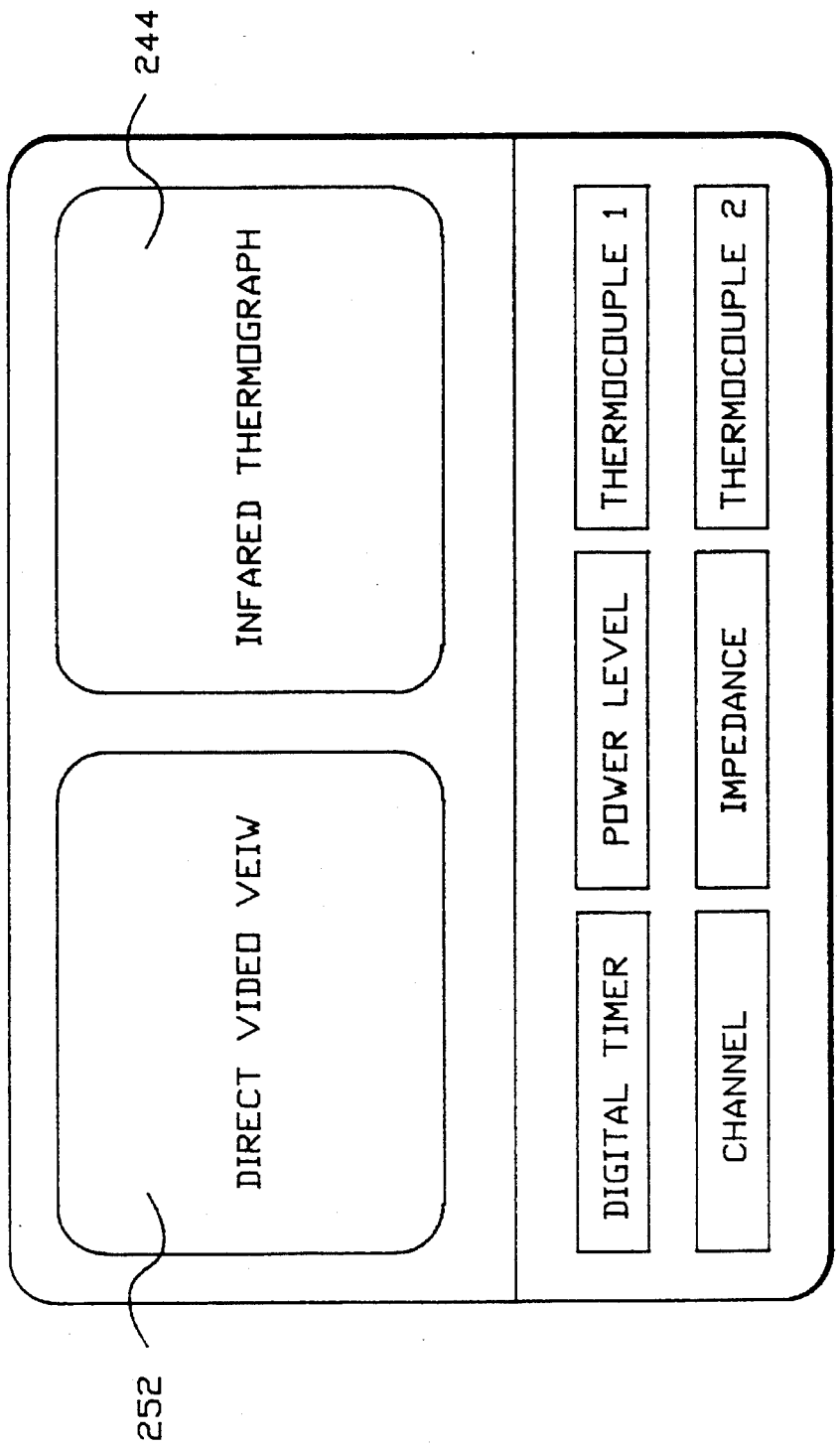
FIG. 18 illustrates a monitor for displaying the various outputs of the ablative apparatus shown in FIG. 17.

FIG. 18 illustrates a monitor screen for displaying the various outputs generated by the apparatus of FIG. 17 so that an operator will know the temperature/resistance characteristics of the specimen at any given time during the RF heating. It will also be possible to develop various algorithms which by experiment would show the various sizes/ shapes of the lesions which can be achieved using given power settings for given amounts of time based on feedback measurements obtained from the tissue, i.e., it is possible to monitor the temperature and rate of rise of the temperature, impedance (resistance to flow of current) and rate of rise of impedance. This process can be done manually by visual inspection, but far superior results will be obtained using a computer-driven algorithm.

The temperature sensing can be performed by thermocouples or thermistors planted within the electrodes in order to monitor the temperature of the electrode during ablation. Also, a temperature sensing device can be placed inside a separate trocar in order to monitor temperatures of the targeted tissue at different locations therein. In this manner, it will be possible to map the rise in temperature via thermal mapping, which can give an indication of the different current conductivities for different tissues depending on their compositions, hydration characteristics, etc.

Figure 19A:
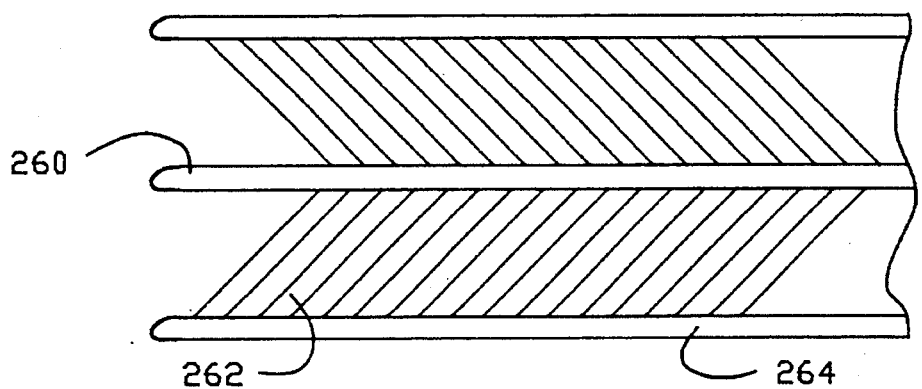
FIG. 19(a) illustrates a further embodiment according to the invention whereby an electrode netting is held within a hollow trocar for deployment out of the trocar and into engagement with an irregular tissue surface.
Figure 19C:
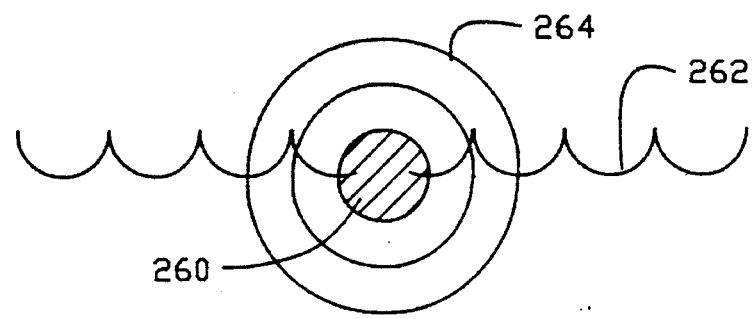
FIG. 19(c) illustrates an end view of the electrode netting attached to the central shaft.
Figure 19D:
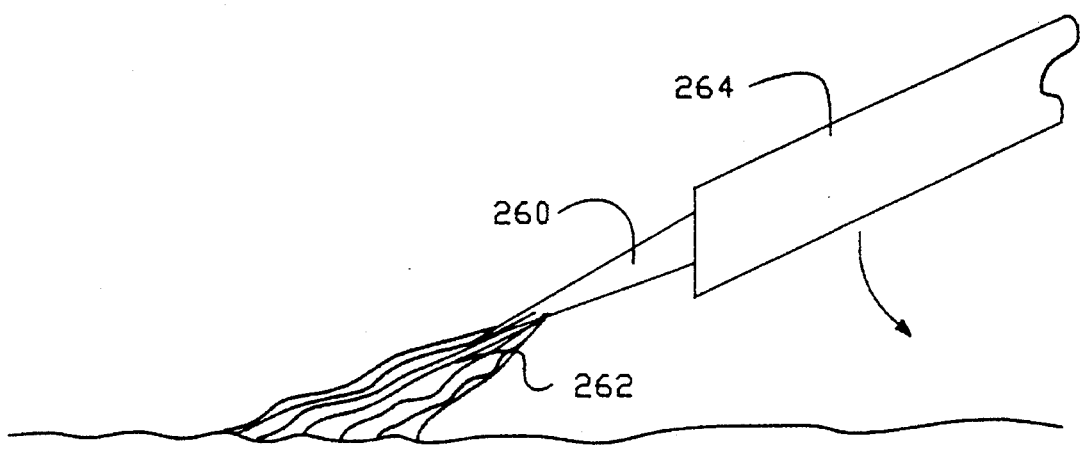
FIG. 19(d) shows the electrode netting in engagement with a tissue surface.
Figure 19B:
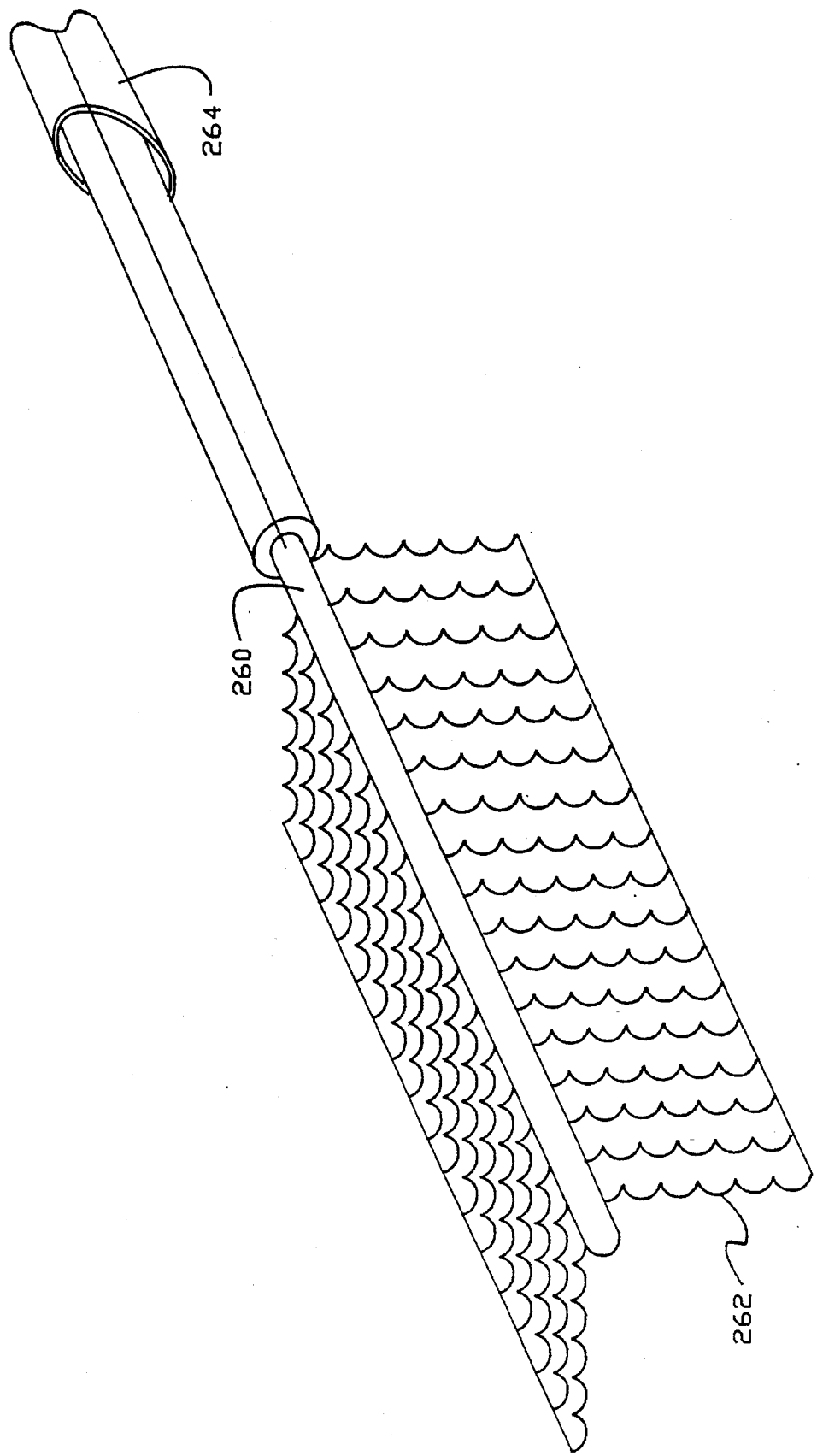
FIG. 19(b) illustrates a perspective view of the embodiment of FIG. 19(a) with the electrode netting shown in the deployed state.

As a further embodiment of the present invention, FIG. 19(a) illustrates an electrode netting which is formed of a flexible metallic material, preferably nickel-titanium wire or stainless steel so that it can be folded up inside a trocar. The flexible netting must be sufficiently pliant so that it can be tightly compressed into a narrow region to allow the trocar to be made as narrow as possible. The netting is formed of nickel titanium or stainless steel with an irregular surface pattern such that when the netting comes into contact with the irregular surface of a lung, for example, the peaks will provide assured electrical contact with the surface tissue. As shown in FIG. 19(b), when the flexible netting is deployed out from the trocar opening, it will expand for subsequent pressure to be applied by the trocar so that the irregular pattern will be pressed against the undulated surface of the tissue. The trocar may enter the lung at a slight angle to the surface to be treated, for example, 15° to the surface to be treated and then pressed with sufficient force against the surface of the targeted tissue. In order to maintain the large number of individual wire portions together, the wires are tied together at their distal ends by laser welding or tig-welding (using titanium with an inert gas). As known, nickel titanium is a "memory alloy" whereby it can be formed into any desired configuration when at an elevated temperature and then when quickly cooled will retain that configuration. When in the relaxed state, deployed out of the trocar, the wires of the netting are spread outwardly with a high tensile yield so that they can be pressed securely into the peaks and valleys of the irregular surface of the tissue. FIGS. 19(c) and 19(d) respectively show an end view of the ablative netting electrode device when in the deployed state, and a side view when in contact with tissue having an irregular surface. The electrode netting can also be used for pressing against other irregular or undulated surfaces such as colon tissue, bladder, stomach, liver, esophagus, etc.

As a further embodiment according to the present invention, in order to obtain larger sized lesions through the ablative process, it has been found desirable to move the electrode back and forth slightly within the tissue in order to delay the onset of desiccation, i.e., dehydration, of the tissue. Such dehydration of the tissue will cause an increase in the impedance between the opposite electrodes because the transfer medium becomes less conductive, which will then cause the current to be cut off and the ablation with RF energy to stop. Therefore, the desiccation of the tissue serves as a type of natural "switch" to end ablation when the tissue dries out. However, it is desirable to maintain the ablation process for as long as possible in order to generate a larger ablation volume, as opposed to a quickly "burned out" smaller region. It has been found through experiments that moving the electrodes back-and-forth 1–3 mm is adequate to extend the ablation period and increase the resulting ablation volume significantly. Initial results indicate that this volume is in the range of 2–3 times greater than that obtained by performing the procedure without electrode movement. Although these initial experiments have involved the movement of the electrode in an axial mode, it is possible that other movements, including rotational or rotation-plus-axial movement may prove to further enhance and lengthen the ablation period of time. It is also possible to apply fluid to the ablation region in order to maintain the tissue sufficiently moisturized so that desiccation does not occur prematurely.

The movement of the electrode can be manual (performed by the operator) or, preferably, incorporated as a function built into the device and not requiring intervention by the operator. In this way, the amount of movement and frequency can be automatic and therefore not subject to oversight or variations. Also, as another means for accomplishing the extended ablative time and preventing early desiccation, additional hydration can be infused through or adjacent to the electrode in order to replace that lost during the ablative process by applying additional hydration in the form of saline or other conductive solution. The electrode may be hollow and have perforations along the active length thereof to allow passage of the solution to the surrounding tissues. In another embodiment, the solution may flow through the space between the inside of the insulating sleeve and the other surface of the electrode. By moving the insulating sleeve to its most distal position, near the distal end of the electrode and dispensing fluid as the insulating sleeve is drawn backward toward the proximal end of the active electrode, fluid can be dispensed along the entire length of the ablating area. In addition, the two methods may be combined in order to further enhance and lengthen the ablated tissue volume.

Figure 20A:
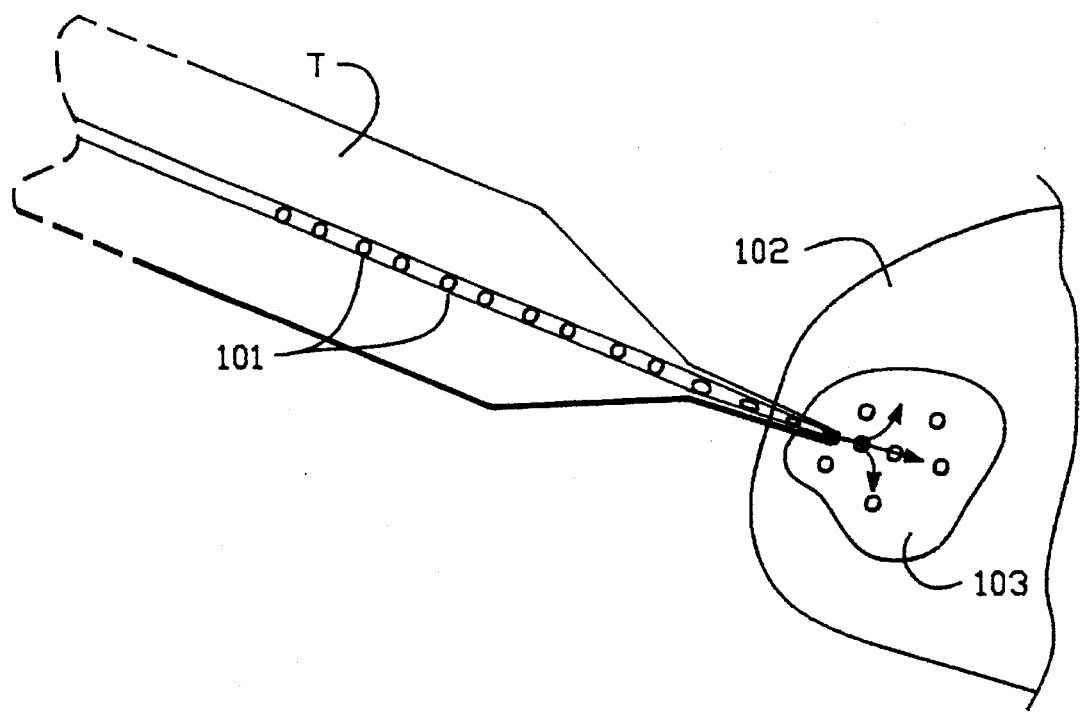
FIG. 20(a) illustrates a further embodiment according to the present invention whereby the chemotherapeutic drugs are administered to a cancerous site using tiny microspheres which contain the therapeutic substances.
Figure 20B:
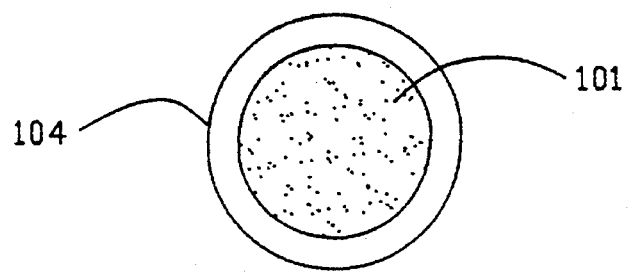
FIG. 20(b) shows an enlarged view of the microspheres with the external coating to be subsequently removed when the therapeutic drugs are to be released within the patient's body.

As shown in FIG. 20(a), another embodiment according to the present invention involves the introduction of a large number of microspheres into a tissue mass so that the microspheres can be targeted in a site specific manner. As shown, the microspheres are supplied through a thin cannula within a trocar T and are injected into the neoplasm 103 within tissue mass 102. The microspheres are tiny hollow metallic spheres with a large number of pores formed therein so that the therapeutic substance can be released through the pores. In order to control the release of the therapeutic substance from inside the microspheres, a thin coating 104 is provided around the entire surface of each of the microspheres 101, and after the microspheres are injected into the neoplasm 103, the substance can be released at any desired time by applying RF energy or inductive electrical energy as a way of "burning off" the coating 104. Alternatively, the coating 104 could be removed by action of a solvent injected into the neoplasm 103 which will chemically strip away the coating 104. Also, the coating 104 could simply be biodegradable for chemical stripping by the body's natural fluids. In this manner, a site specific application of the therapeutic drug within the neoplasm can be achieved, as well as an accurately controlled timed release of the drugs into the neoplasm. The drug will be delivered to and within the tumor by injection or infusion through a device for tissue ablation, such as described in previous co-pending applications 08/148,439 and 08/148,441. Also, the microspheres may be injected using ordinary hyperdermic syringes and/or needles. After infusion into the tissue to be treated, the metallic microspheres can be heated by induction using RF energy via appropriate induction coils or other antenna means. The size of the microspheres will be small enough to be carried out of the body through normal filtration and excretion functions of the kidney and urinary system. This range will generally be from 20 to 10,000 microns in diameter, and the material used for the hollow microspheres can be a resin material coated with a thermally sensitive film constituting the coating 104 for sealing the drug within the microspheres, such as, for example, polyglactic acid, polyglycolic acid, etc. Also, this delivery system could be used to carry other compounds such as contrast agents, antibiotics, etc., where it is desirable to limit the areas to which the compounds are delivered.

Another delivery system according to the present invention for delivering therapeutic substances to a tumor or tumors in a site specific manner is illustrated in FIG. 21. As shown, a plurality of capillary tubes 180 are provided within the plurality of cancer sites 182 in order to provide a supply means for supplying therapeutic substances from an external pump which is located outside of the patient's body within the room in which the patient is located, or alternatively, the pump can be mounted to the patient's body, similar to insulin delivery pumps currently available. As shown in FIG. 21, a trocar T receives the therapeutic substances from the pump in the direction of arrow z via a tubing 186 and then distributes the substance via a coupling tubing 184 to the plurality of capillaries 180. The capillaries are securely held to the cancer sites, via surgical barbs 188. The barbs keep the capillary tubes 180 from pulling out of the cancer sites 182. This "plumbing delivery" system has important advantages over conventional systemic delivery systems which supply the therapeutic compounds to all parts of the patient's body. Conventional systemic delivery leads to the significant side effect associated with chemotherapy such as hair loss, nausea, digestive problems, etc., and affects many parts of the body for which no treatment is desired. The very site specific delivery method shown in FIG. 21 overcomes such drawbacks. The capillaries 180 could be made from small diameter "micro" tubing. In conventional chemotherapy, treatment with the drugs usually takes several months because the patient first undergoes a week or so of taking the drugs, and then is required to rest for several days because of the adverse side effects of the drugs. Then the cycle continues again for another week of taking the drugs, and then the rest period, etc. With the method of FIG. 21, on the other hand, there will be much less trauma to the patient because of the localized manner of the delivery and much smaller quantity required than when delivered systemically. In this case, it may be possible that the patient only has to be treated with the therapeutic compounds for a single week after the localized ablation techniques described above. In other words, the localized ablation techniques will be used to remove most of the cancerous cells, and then the therapeutic delivery methods can be used as a type of clean-up operation to destroy any remaining cancerous cells. The pump used for supplying the therapeutic substances to the cancer sites can be microprocessor controlled with a built-in clock so as to deliver the compounds to the cancerous sites at controlled times.

The capillaries 180 are held at the cancerous sites and then taken out when the treatment is completed. Also, the capillaries 180 could be made out of a re-absorbable material such as polyglactic acid so that they will be absorbed by the body and eliminated. Alternatively, the capillaries 180 could be manually removed. However, it may be more desirable to use re-absorbable materials so that the capillaries do not have to be removed which could lead to the possibility of "seeding" cancerous cells throughout the path of withdrawal in the event that any cancerous cells are picked up by the ends of the capillaries 180 held in the cancerous sites 182.

As a further clean-up operation, the device shown in FIG. 22 is used as a type of whipping device for liquefying ablated tissue prior to removal from the body. Using radio frequency energy to ablate tumors within the human body often leads to considerable amounts of dead tissue left for removal by the microphage activity. This has a disadvantage of requiring considerable body activity for removing this dead tissue and thus overloads the ability of the kidney and immune system to handle these by-products. In the case of certain organs, it has been shown that the radio frequency energy tends to soften and emulsify the tissue. The embodiment of FIG. 22 would be used to liquify the dead tissue so that it can be subsequently removed by suctioning and/or flushing, followed by the introduction of antibiotic and antishock drugs to help the body recover from the trauma of the procedure. This debris removal and cleaning procedure may also help to prepare the site for introduction of reconstructive materials such as collagen, etc.

As shown in FIG. 22, a small wire or monofilament loop is introduced through the hollow trocar needle of the ablative device. When placed within the ablative tissue, the wire loop would be spun in the manner of a whip, for the liquefying the ablative tissue. Because the wire or monofilament loop will be designed to be soft enough so that only the ablated or already partially liquified tissue will be affected by the twirling motion of the loop. However, when the loop comes in contact with unablated tissue, no liquification or damage to the tissue will occur.

To those skilled in the art to which this invention relates, many changes in construction and widely differing embodiments and applications of the invention are within the skill of the art and are intended to be included within the scope of this application.

What is claimed as new and is desired to be secured by Letters Patent of the United States is:

1. A method for ablating tissue at a tissue treatment site where dehydration of tissue at the tissue treatment site is reduced, the method comprising the steps of:

a) introducing an Rf ablation device into a tissue treatment site, the device including a hollow tubular Rf electrode having a closed, sharpened distal tip, an electrode conductive surface for conducting Rf ablation, and a plurality of fluid distribution ports distributed along the length of the electrode for delivering chemotherapeutic agents to the tissue treatment site; and b) supplying Rf power to the electrode to produce a diffusion barrier capsule at the tissue treatment site wherein the position of the electrode relative to the tissue treatment site is varied sufficiently frequently to reduce dehydration of tissue at the tissue treatment site.

2. The method according to claim 1, further including the step of passing fluid through the fluid distribution ports during ablation to reduce dehydration of tissue at the tissue treatment site.

3. The method according to claim 1 further including the step of varying the position of the electrode relative to the tissue treatment site by at least 1 mm during ablation.

4. The method according to claim 2 further including the step of varying the position of the electrode relative to the tissue treatment site between about 1 and 3 mm.

5. The method according to claim 1 further including the step of varying the position of the electrode relative to the tissue treatment site along a longitudinal axis of the electrode.

6. The method according to claim 1 wherein the device further includes an electrode position modifier and further including the step of varying the position of the electrode relative to the tissue treatment site sufficiently frequently during ablation to reduce dehydration of tissue at the tissue treatment site.

7. The method according to claim 5 further including the step of passing fluid through the fluid distribution ports during ablation to reduce dehydration of tissue at the tissue treatment site.

8. The method according to claim 7 further including the step of varying the position of the electrode relative to the tissue treatment site is by at least 1 mm during ablation.

9. The method according to claim 8 further including the step of varying the position of the electrode relative to the tissue treatment site by between about 1 and 3 mm.

* * * * *